US00RE43283E

(19) United States
(12) Reissued Patent
Ishida et al.

(10) Patent Number: US RE43,283 E
(45) Date of Reissued Patent: *Mar. 27, 2012

(54) BLOOD COLLECTING APPARATUS AND BLOOD COLLECTING METHOD USING BLOOD COLLECTING APPARATUS

(75) Inventors: Noboru Ishida, Fujinomiya (JP); Yoshihiro Yokoo, Fujinomiya (JP); Hitoshi Kuroki, Fujinomiya (JP)

(73) Assignee: Terumo Kabushiki Kaisha, Shibuya-Ku, Tokyo (JP)

( * ) Notice: This patent is subject to a terminal disclaimer.

(21) Appl. No.: 12/371,210

(22) Filed: Feb. 13, 2009

Related U.S. Patent Documents

Reissue of:
(64) Patent No.: 6,592,613
Issued: Jul. 15, 2003
Appl. No.: 09/613,273
Filed: Jul. 10, 2000

U.S. Applications:
(63) Continuation-in-part of application No. 09/231,782, filed on Jan. 15, 1999, now Pat. No. 6,328,726.

(30) Foreign Application Priority Data

Jan. 16, 1998 (JP) ..... 10-020394
Jul. 9, 1999 (JP) ..... 11-195835

(51) Int. Cl.
*A61B 19/00* (2006.01)

(52) U.S. Cl. ..... 604/408; 604/401; 604/501; 604/502; 604/503

(58) Field of Classification Search ..... 604/4–6, 604/244, 408, 410, 262, 401, 501, 502, 503
See application file for complete search history.

(56) References Cited

U.S. PATENT DOCUMENTS
4,846,795 A 7/1989 Minagawa
(Continued)

FOREIGN PATENT DOCUMENTS
EP 455215 * 6/1991
(Continued)

OTHER PUBLICATIONS
H. Olthuis et al., "A Simple Method To Remove Contaminating Bacteria During Venepuncture," *Vox Sanguinis International Journal of Transfusion Medicine, 24th Congress of the International Society of Blood Transfusion,* Abstract 1/2C-33 OP, Suppl 2, 1996, p. 113, S. Karger Medical and Scientific Publishers.
(Continued)

*Primary Examiner* — Shawntina Fuqua
*Assistant Examiner* — Vinod D Patel
(74) *Attorney, Agent, or Firm* — Buchanan Ingersoll & Rooney PC

(57) ABSTRACT

A blood collecting apparatus comprises a blood collecting needle 152; the blood collecting bag, a first tube whose one end communicates with the blood collecting bag and other end communicates with the blood collecting needle, the branch portion provided on a portion of the first tube, a second tube connected with the branch portion at one end thereof and having a blood take-out port (sampling port); and a flexible resin bag including a third tube communicating with the second tube. The flexible resin bag is capable of accommodating air inside a part of the first tube between the branch portion and the blood collecting needle and air inside the second tube when the blood collecting apparatus is used.

30 Claims, 18 Drawing Sheets

U.S. PATENT DOCUMENTS

| | | | |
|---|---|---|---|
| 5,098,371 | A | 3/1992 | Juji et al. |
| 5,518,005 | A | 5/1996 | Brannon |
| 6,328,726 | B1 | 12/2001 | Ishida et al. |

FOREIGN PATENT DOCUMENTS

| | | | |
|---|---|---|---|
| EP | 0 455 215 | A2 | 11/1991 |
| JP | 63-132658 | A | 6/1988 |
| JP | 2-71728 | A | 3/1990 |
| JP | 2-167173 | A | 6/1990 |
| JP | 4-187156 | A | 7/1992 |
| JP | 5-28341 | U | 4/1993 |
| JP | 5-220201 | A | 8/1993 |
| JP | 6-285157 | A | 10/1994 |
| JP | 8-173405 | A | 7/1996 |
| JP | 10-84942 | A | 4/1998 |
| JP | 10-211274 | A | 8/1998 |
| WO | 83/00813 | * | 3/1983 |
| WO | WO 83/00813 | A1 | 3/1983 |
| WO | 89/09025 | * | 10/1989 |
| WO | WO 89/09025 | A1 | 10/1989 |
| WO | WO 98/28057 | A1 | 7/1998 |

OTHER PUBLICATIONS

"NIH Holds Microbial Contamination Workshop," *Blood Bank Week,* Sep. 29, 1995, pp. 1-3, vol. 12, No. 36, American Association of Blood Banks.

"NIH Workshop Examines Bacterial Contamination of Blood Components," *CCBC Newsletter,* Oct. 13, 1995, pp. 13-17, Council of Community Blood Centers.

* cited by examiner

BLOOD COLLECTING APPARATUS AND BLOOD COLLECTING METHOD USING BLOOD COLLECTING APPARATUS

Matter enclosed in heavy brackets [ ] appears in the original patent but forms no part of this reissue specification; matter printed in italics indicates the additions made by reissue.

This application is a continuation-in-part of U.S. application Ser. No. 09/231,782, filed on Jan. 15, 1999, the entire content of which is incorporated herein by reference, and claims priority under 35 U.S.C. §120 with respect to such U.S. application.

BACKGROUND OF THE INVENTION

The present invention relates to a blood collecting apparatus and a blood-collecting method to be carried out by using the blood collecting apparatus.

In normal blood collecting (operation of introducing blood collected from a donor by a blood collecting needle into a blood collecting bag), a needle-piercing portion of the donor is sterilized with alcohol. But there is a possibility that bacteria present on or under the skin enters the blood collecting bag together with the blood.

Some kinds of bacteria which have entered the blood collecting bag increase while the blood collecting bag is kept cold. When the blood is transfused into a patient, the patient may suffer from infectious disease or blood poisoning.

The pH of red blood cell conservation liquid (S.A.G.M. liquid, OPTISOL liquid, M.A.P. liquid, and the like) currently used is substantially neutral, unlike the conventional blood conservation liquid (anticoagulants such as ACD-A liquid and CPD liquid). Thus, in the red blood cell conservation liquid, bacteria increase in a high extent while the blood collecting bag is refrigerated.

Because the bacteria are present not only on the skin but also under the skin, only careful sterilization of the needle-piercing portion is not enough to prevent them from penetrating into blood.

It is experimentally known that bacteria penetrates into an initial flow of collected blood, together with fragments of skin. However, a blood collecting bag or a blood collecting apparatus capable of removing the initial flow of collected blood has not been developed.

It is an object of the present invention to provide a blood collecting apparatus and a blood-collecting method to be carried out by using the blood collecting apparatus capable of preventing blood from being contaminated with bacteria, improving safety, and collecting examination blood in a preferable state.

SUMMARY OF THE INVENTION

In order to achieve the object, there is provided a blood collecting apparatus comprising a blood collecting needle for collecting blood from a donor, a blood collecting bag for accommodating collected blood, a first tube whose one end communicates with said blood collecting bag and other end communicates with said blood collecting needle, a branch portion provided on a portion of said first tube, a second tube connected with said branch portion at one end thereof and having a blood take-out port, and a flexible resin bag and having a third tube communicating with said second tube.

In order to further achieve the object, there is provided a blood collecting apparatus comprising a blood collecting needle for collecting blood from a donor, a blood collecting bag for accommodating collected blood, a first tube whose one end communicates with said blood collecting bag and other end communicates with said blood collecting needle, a branch portion provided on a portion of said first tube, a second tube connected with said branch portion at one end thereof and having a blood take-out port, and a filter gas-permeable and blood-unpermeable and communicable with an interior of said second tube.

In order to further achieve the object, there is provided a blood collecting apparatus comprising, a blood collecting needle for collecting blood from a donor, a blood collecting bag for accommodating collected blood, a first duct whose one end communicates with said blood collecting bag and other end communicates with said blood collecting needle, and introducing said collected blood into said blood collecting bag, a second duct branching from said first duct through a branch portion and having a blood take-out port, and pressure buffering means for suppressing fluctuation of a pressure of said second duct.

In order to further achieve the object, there is provided a blood collecting method to be carried out by using a blood collecting apparatus comprising: a blood collecting needle for collecting blood from a donor; a blood collecting bag for accommodating collected blood; a first tube whose one end communicates with said blood collecting bag and other end communicates with said blood collecting needle; a branch portion provided on a portion of said first tube; a second tube connected with said branch portion at one end thereof and having a blood take-out port at the other end thereof; and a flexible resin bag and having a third tube communicating with said second tube, said blood collecting method comprising the steps of piercing a blood collecting needle into a donor when a portion of said first tube positioned between said branch portion and said blood collecting bag is sealed, removing air inside said first and second tubes by introducing an initial flow blood from said donor into a portion of said first tube between said blood collecting needle and said branch portion and into said second tube and by accommodating air inside said portion of the first tube positioned between said blood collecting needle and said branch portion and air inside said second tube in said flexible resin bag; and collecting a predetermined amount of blood from said donor in said blood collecting bag by intercepting communication between said first tube and said flexible resin bag and by communicating said portion of said first tube between said blood collecting needle and said branch portion with a portion of said first tube between said branch portion and said blood collecting bag.

In order to further achieve the object, there is provided a blood collecting method to be carried out by using a blood collecting apparatus comprising a blood collecting needle for collecting blood from a donor; a blood collecting bag for accommodating collected blood; a first tube whose one end communicates with said blood collecting bag and other end communicates with said blood collecting needle; a branch portion provided on a portion of said first tube; a second tube connected with said branch portion at one end thereof and having a blood take-out port at the other end thereof; and a filter gas-permeable and blood unpermeable and communicable with an interior of said second tube, said blood collecting method comprising the steps of piercing a blood collecting needle into a donor when a portion of said first tube positioned between said branch portion and said blood collecting bag is sealed, exhausting air inside said first and second tubes from said filter by introducing an initial flow blood from said donor into a portion of said first tube between said blood collecting needle and said branch portion and into said second tube, collecting a predetermined amount of blood from said donor in said blood collecting bag by intercepting communication between said first tube and said filter and by communicating said portion of said first tube between said blood collecting needle and said branch portion with a portion of said first tube between said branch portion and said blood collecting bag.

In order to further achieve the object, there is provided a blood collecting apparatus comprising, a blood collecting needle for collecting blood from a donor, a blood collecting bag for accommodating collected blood, a first duct whose one end communicates with said blood collecting bag and other end communicates with said blood collecting needle to introduce said collected blood into said blood collecting bag, a second duct branching from said first duct through a branch portion and having a blood take-out port and an accommodating portion, provided on said second duct, for accommodating said collected blood temporarily.

In order to further achieve the object, there is provided a blood collecting apparatus comprising, a blood collecting needle for collecting blood from a donor, a blood collecting bag for accommodating collected blood, a first duct whose one end communicates with said blood collecting bag and other end communicates with said blood collecting needle to introduce said collected blood into said blood collecting bag, a second duct branching from said first duct through a branch portion and having a blood take-out port and an accommodating portion, provided on a second duct at a portion between said branch portion and said blood take-out port, for accommodating said collected blood.

DETAILED DESCRIPTION OF THE PREFERRED EMBODIMENTS

Figure 1:
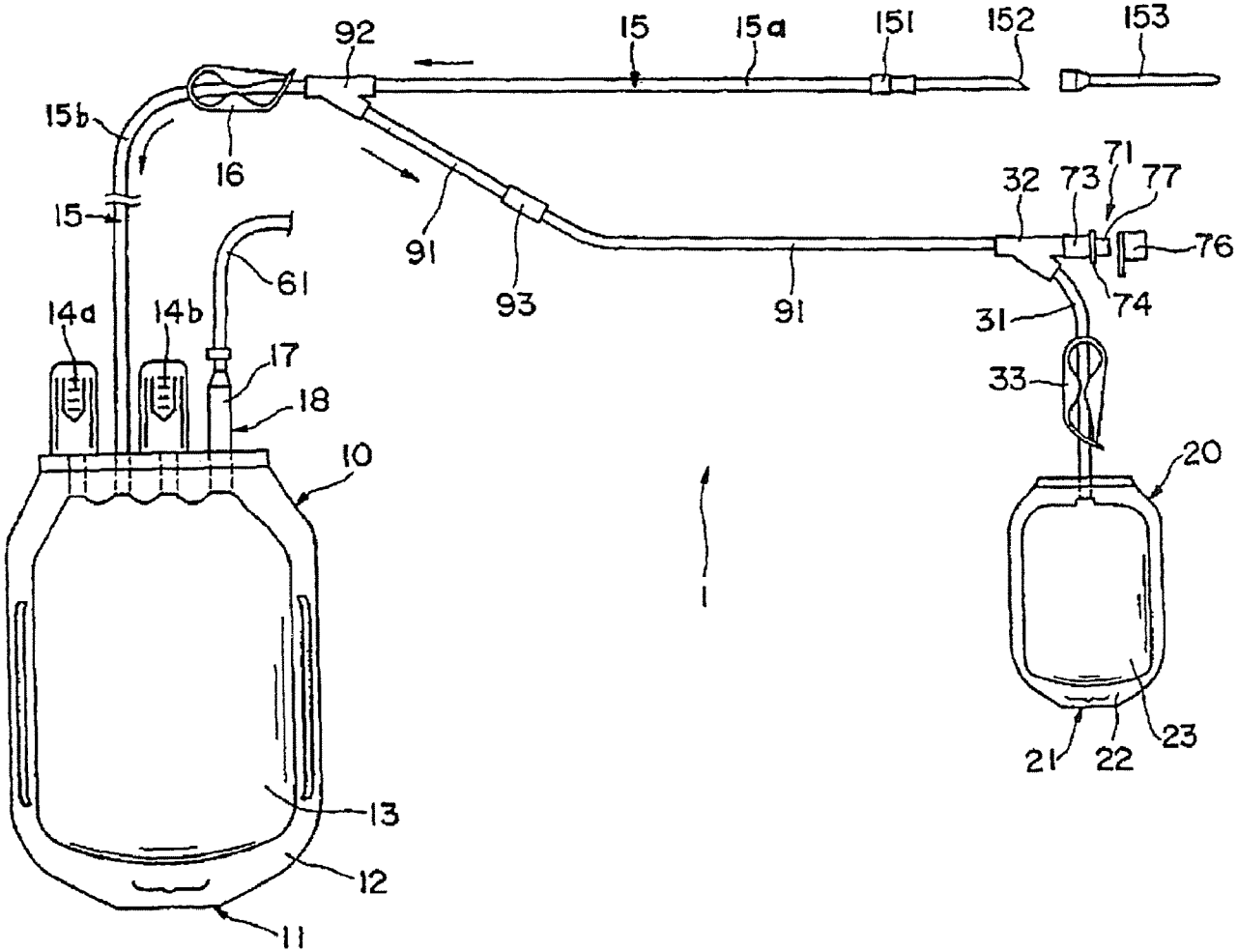
FIG. 1 is a plan view showing a first embodiment of the blood collecting apparatus of the present invention.

The preferred embodiments of the blood collecting apparatus of the present invention will be described in detail below.

Each of the blood collecting apparatus 1, 1a, 1b, 1c, 1d, 1e, and 1f of the present invention comprises a blood collecting needle 152 for collecting blood from a donor; a blood collecting bag 10 for accommodating collected blood; a first duct whose one end communicates with a blood collecting bag 10 and other end communicates with a blood collecting needle 152 and introducing collected blood into the blood collecting bag 10; a second duct branching from the first duct through a branch portion and having a take-out port of blood at an end thereof. Each of the blood collecting apparatus 1, 1a, 1b, 1c, 1d, 1e, and 1f comprises a pressure buffering means for suppressing the fluctuation of the pressure of the second duct.

More specifically, each of the blood collecting apparatus 1, 1c and 1f of the present invention comprises the blood collecting needle 152 for collecting blood from a donor; the blood collecting bag 10 for accommodating collected blood; a first tube 15 (15a, 15b) whose one end communicates with the blood collecting bag 10 and other end communicates with the blood collecting needle 152; the branch portion 92 provided on a portion of the first tube 15; a second tube 91 connected with the branch portion 92 at one end thereof and having a blood take-out port (sampling port) 71 at the other end thereof; and a flexible resin bag 20 and having a third tube 31 communicating with the second tube 91. The flexible resin bag 20 including the third tube 31 is capable of accommodating air inside a part of the first tube 15 (first tube 15a at the side of the blood collecting needle 152) between the branch portion 92 and the blood collecting needle 152 and air inside the second tube 91 when the blood collecting apparatus is used.

FIG. 1 is a plan view showing a first embodiment of the blood collecting apparatus of the present invention. As shown in FIG. 1, the blood collecting apparatus 1 has a blood collecting bag 10 for accommodating collected blood.

The blood collecting bag 10 has a body 11 formed by fusing (heat fusion, high frequency fusion or the like) or bonding to each other the periphery of a sealing portion 12 of two sheet materials made of a flexible soft resin such as polyvinyl chloride and laminated on each other, as will be described later.

A blood-accommodating portion 13 accommodating collected blood is formed at an inner portion surrounded with the sealing portion 12 of the body 11. The blood collecting bag 10 may be used as a red blood cell bag for preserving red blood cells. In this case, the blood-accommodating portion 13 accommodates and stores red blood cell rich liquid.

Two openings 14a and 14b each sealed with a peel tab are formed at an upper portion of the body 11 such that they can be opened. An outlet port 18 is formed alongside of the opening 14b. The outlet port 18 is connected with one end of a tube 61 through a sealing member 17 (connection member).

As the sealing member 17, it is possible to use a member having a construction similar to that of a sealing member 93 that will be described later.

Although not shown in FIG. 1, one or more bags such as a blood plasma bag, a buffy coat bag, a platelet bag (medical fluid-storing bag) may be provided at the other end of the tube 61. That is, the blood collecting apparatus 1 may constitute a bag-connected device.

In the present invention, it is possible to omit the provision of the sealing member 17, the outlet port 18, and the tube 61.

One end of the flexible first tube 15 communicating with the blood-accommodating portion 13 is connected with the body 11 at an upper portion thereof. A blood collecting needle 152 is installed at the other end of the first tube 15 through a hub 151. A cap 153 which is to cover the blood collecting needle 152 is installed on the hub 151. A main part of the first duct is composed of the lumen of the first tube 15.

The first branch connector 92 (branch portion) branching bifurcately is provided at a portion of the first tube 15. For example, the first branch connector 92 (branch portion) is located at an intermediate portion of the first tube 15 or at the side of the blood collecting bag 10 of the first tube 15. One end of the flexible second tube 91 is connected with the first branch connector 92. A main part of the second duct is composed of the lumen of the second tube 91. The first tube 15 comprises a first tube 15a which is positioned at the side of the blood collecting needle 152 with respect to the first branch connector 92 and a first tube 15b which is positioned at the side of the blood collecting bag 10 with respect to the first branch connector 92.

Although the first branch connector 92 shown in FIG. 1 consists of a y-shaped tube, the first branch connector 92 of the present invention may be Y-shaped, T-shaped or inverse y-shaped.

A clamp (first duct-sealing member) 16 is provided on a portion of the first tube 15 between the first branch connector 92 and the blood collecting bag 10. That is, the clamp 16 is provided on the first tube 15b located at the side of the blood collecting bag 10 with respect to the first branch connector 92. Preferably, the clamp 16 is positioned proximately to the first branch connector 92.

A second branch connector (branch portion) 32 branching bifurcately is provided at the other end of the second tube 91. The second branch connector 32 is connected with a sampling port (connector) 71 constituting a blood take-out port. The construction of the sampling port 71 will be described in detail later.

Although the second branch connector 32 shown in FIG. 1 consists of a y-shaped tube, the second branch connector 32 of the present invention may be Y-shaped, T-shaped or inverse y-shaped.

In the blood collecting apparatus 1, the sampling port 71 is connected with the other end of the second tube 91 through the second branch connector 32. It is possible to position the second branch connector 32 at a portion of the second tube 91 between both ends thereof and directly connect the sampling port 71 with the other end of the second tube 91. The sampling port (blood take-out port) 71 may be provided at a portion of the second tube 91. For example, the sampling port (blood take-out port) 71 may be provided at a intermediate portion of the second tube 91 or at the other end side of the second tube 91.

A sealing member (second duct-sealing member) 93 is provided at a portion of the second tube 91. In this case, preferably, the sealing member 93 is positioned proximately to the first branch connector 92. The construction of the sealing member 93 will be described in detail later.

The blood collecting apparatus 1 has a flexible resin bag 20 for suppressing fluctuation of pressure.

The flexible resin bag 20 has a body 21 formed by fusing (heat fusion, high frequency fusion or the like) or bonding to each other the periphery of a sealing portion 22 of two sheet materials made of a flexible soft resin such as polyvinyl chloride and laminated on each other, as will be described later.

The body 21 has an accommodating portion 23 formed in an inner part thereof surrounded with a sealing portion 22 thereof.

One end (termination) of a flexible third tube 31 communicating with the accommodating portion 23 is connected with the body 21 at an upper portion thereof. The other end of the third tube 31 is connected with the second branch connector 32. A main part of the third duct is composed of the lumen of the third tube 31.

The capacity of the bag 20 is not limited to a specified one but determined in consideration of various conditions such as the spatial volume (capacity) of the lumen of the tubes forming the circuit. It is favorable to set the capacity of the bag 20 to 1-100 ml and more favorable to 5-30 ml. If the capacity of the bag 20 is less than the lower limit of the above-described range, the effect of the bag 20 which will be described later may not be obtained when the spatial volume of the lumen of the tube forming the circuit is comparatively large. On the other hand, if the capacity of the bag 20 is more than the upper limit of the above-described range, the blood collecting apparatus 1 is caused to be large.

The flexible resin bag 20 including the third tube 31 is capable of accommodating air inside the first tube 15a at the side of the blood collecting needle 152 and air inside the second tube 91 when the blood collecting apparatus is used.

A clamp (third duct-sealing member) 33 is provided on the third tube 31. Preferably, the clamp 33 is positioned proximately to the second branch connector 32 to prevent reduction of the amount of an initial flow of collected blood (hereinafter referred to as initial flow blood or initial introduced blood) which can be introduced into a first vacuum blood collecting tube 85 which will be described later.

In the blood collecting apparatus 1, a pressure buffering means for preventing fluctuation of the pressure in the second duct is constituted of the second branch connector 32, the third tube 31, the clamp 33, and the bag 20.

It is preferable to set the area of the sectional surface of the duct of the second tube 91 smaller than that of the sectional surface of the first tube 15. That is, it is preferable to set the inner diameter of the second tube 91 smaller than that of the first tube 15 to allow collected blood to be left in a small amount in the second tube 91 in introducing collected blood into the blood collecting bag 10, as will be described later.

It is preferable to put an anticoagulant agent in the blood collecting bag 10 in advance. Normally, the anticoagulant agent is a liquid. An ACD-A liquid, a CPD liquid, and a CPDA-1 liquid, and a heparin sodium liquid can be used as the anticoagulant agent The amount of the anticoagulant agent is appropriately determined according to an amount of blood to be collected.

The sheet material composing the blood collecting bags 10 and 20 and the material composing the first tube 15, the third tube 31, the tube 61, and the second tube 91 will be described below.

[1] Material of Blood Collecting Bag 10

The composition, characteristic, and the like of the material of the sheet composing the body 11 of the blood collecting bag 10 are not limited to specified ones.

In this case, as the sheet material composing the blood collecting bag 10, soft polyvinyl chloride or materials containing the soft polyvinyl chloride as their main component can be preferably used. For example, a copolymer containing the soft polyvinyl chloride as its main component and a small amount of macromolecular material, a polymer blend, a polymer alloy, and the like can be used.

As the plasticizer for the soft polyvinyl chloride, dioctylphthalate (DEHP, di(2-ethylhexyl)phthalate) and (DnDP, di(n-decyl)phthalate) can be preferably used.

It is favorable to contain the plasticizer in the sheet material at 25-50 wt % and more favorable at 30-40 wt %. The above-described sheet materials can be manufactured by a method described below.

Using a kneader, materials are kneaded sufficiently. Then, a kneaded material is extruded through a T-shaped die or a circular die. Then, a resulting flat sheet-shaped material is processed into a desired shape/form by sequentially performing the steps of thermoforming, blowing, drawing, cutting, and sealing (fusing) of the edge thereof.

In order to prevent blocking from occurring between sheets (base material), it is possible to roughen (emboss) the surface of each sheet or add or apply a blocking-preventing agent, a slip agent or the like to the materials.

[2] Material of Flexible Resin Bag 20

The composition, characteristic, and the like of the sheet material composing the body 21 of the bag 20 are not limited to specified ones, For example, materials similar to the sheet material of the blood collecting bag 10 may be used to form the bag 20. In this case, the kind of sheet material to be prepared can be reduced, which is advantageous in manufacturing the bag 20.

[3] Materials of Tubes 15, 31, 61, and 91

As the material of the tubes 15, 31, 61, and 91, thermoplastic elastomers or thermoplastic flexible resin such as soft polyvinyl chloride, polyethylene, polypropylene, ethylene-vinyl acetate copolymer, styrene-butadiene-styrene copolymer, and materials containing the thermoplastic elastomers or the thermoplastic flexible resin. The soft polyvinyl chloride and a material containing the soft polyvinyl chloride as its main component are preferable.

The tubes 15, 31, 61, and 91 made of the soft polyvinyl chloride can be handled easily because they are flexible and pliable and can be suitably sealed with a clamp or the like. Further, because the soft polyvinyl chloride is compatible with the sheet material of the bags 10 and 20, the tube made of the soft polyvinyl chloride and the sheet material of the bags 10 and 20 can be fused or bonded to each other at a high degree. Furthermore, the tube made of the soft polyvinyl chloride has a high degree of airtightness. In addition, the tube made of the soft polyvinyl chloride is durable for centrifuging operation and preferably maintains sterility. The kind of plasticizer to be used for the tubes is not specified. The content thereof is also not specified.

The sizes such as the inner and outer diameters of the second tube 91 are not specified. But if the inner diameter thereof is too large or the thickness thereof is too small (ratio of outer diameter to inner diameter is small), the second tube 91 is likely to be flatly deformed when high pressure-steam sterility is performed. This is because the second tube 91 is soft and sealed with the sealing member 93 and a cap 76 which will be described later.

If the inner diameter of the second tube 91 is comparatively large, the spatial volume (volume) of the lumen of the second tube 91 is large accordingly. Consequently, blood loss may occur because of the large spatial volume when collecting of an initial flow blood or an initial introduced blood (hereinafter referred to as initial blood collection) and subsequent (main) blood collection are performed.

As a measure to solve the problem of the volume inside the second tube 91, it is conceivable to adopt a method of using the second tube 91 having small inner and outer diameters. But there is a limitation in the reduction of the outer diameter of the second tube 91 because it is necessary to connect (join) the second tube 91 with other members. Further, the method is incapable of preventing deformation of the second tube 91 sufficiently in the high pressure-steam sterilization.

Accordingly, to solve such a problem effectively, it is favorable to set the inner diameter of the second tube 91 to 0.5-2.0 mm and more favorable to 0.8-1.5 mm. It is also favorable to set the outer diameter thereof to 2-4 times as large as the inner diameter thereof and more favorable to 2.5-3.5 times as large as the inner diameter thereof.

If the inner diameter of the second tube 91 exceeds the upper limit of the above-described range, the amount of air to be exhausted from the second tube 91 increases in the initial blood collecting into the vacuum blood collecting tube 85 which will be described later. Thus, it is necessary to shorten the second tube 91 or increase the volume of the bag 20.

If the inner diameter of the second tube 91 is less than the lower limit of the above-described range, blood is prevented from smoothly flowing in the initial blood collecting into the vacuum blood collecting tube 85. That is, there is a possibility that the flow rate of the blood is insufficient. It is preferable that the flow rate of blood is in the range of 1-5 ml/sec.

The outer diameter of the second tube 91 most suitable in the connection thereof with other members is preferably in the range of 4.0-4.5 mm.

The construction of each of the sealing members 17 and 93 will be described below. The constructions of the sealing members 17 and 93 are similar to each other. Thus, the construction of the sealing member 93 will be described below representatively.

Figure 2:
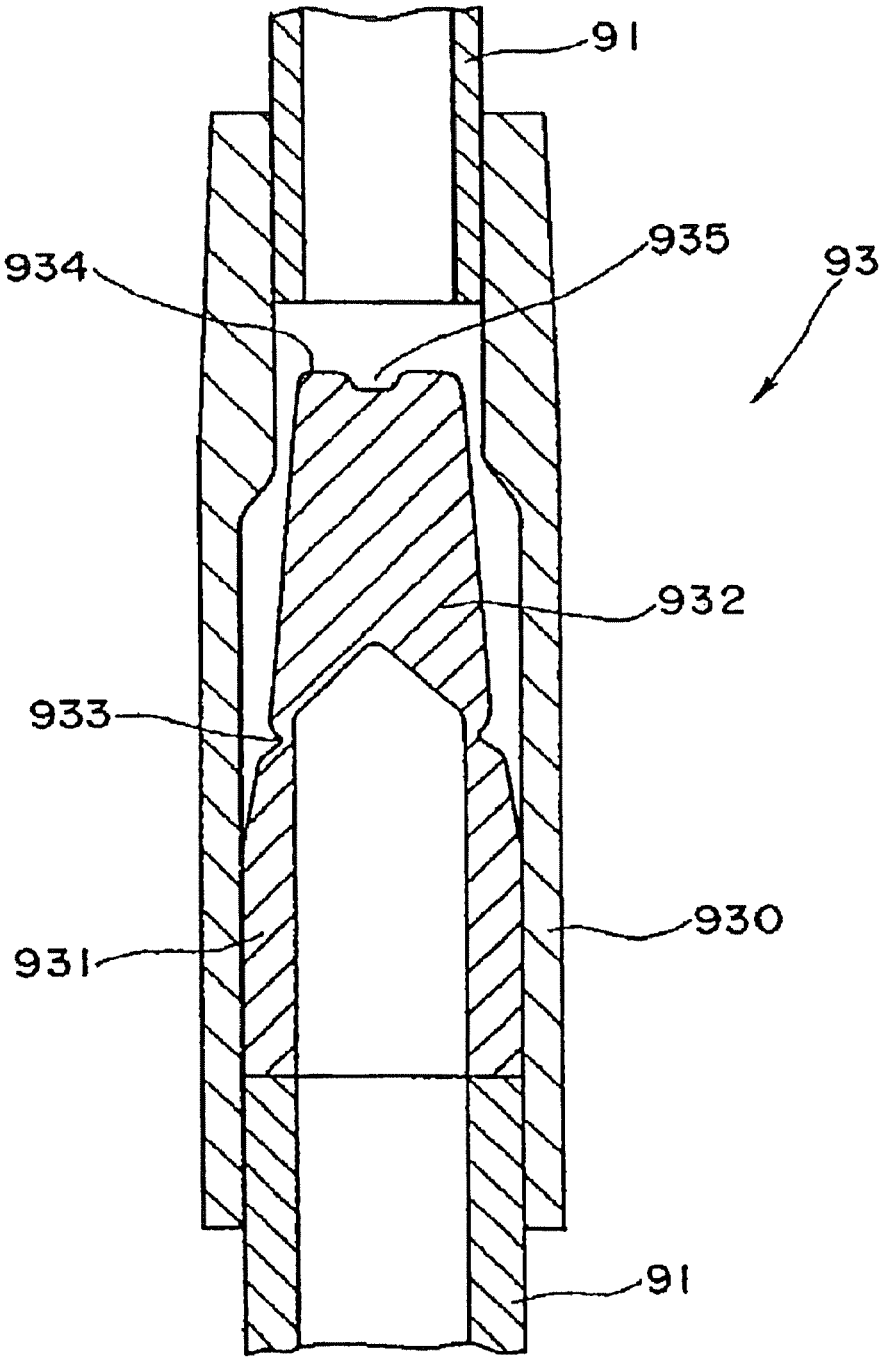
FIG. 2 is a vertical sectional view showing an example of the construction of a sealing member to be used for the blood collecting apparatus of the present invention.

FIG. 2 is a longitudinal sectional view showing an example of the construction of the sealing member 93. As shown in FIG. 2, the sealing member 93 comprises a short tube 930 made of a flexible resin such as soft polyvinyl chloride and a cylindrical body 931 which is liquid-tightly inserted into the short tube 930 and whose one end is sealed with a solid columnar portion 932.

One end of the second tube 91 positioned at an upper side in FIG. 2 is liquid-tightly connected with the upper end of the short tube 930. One end of the second tube 91 positioned at a lower side in FIG. 2 is liquid-tightly connected with the lower end of the short tube 930.

A thin and frail breakable portion 933 is formed on the periphery of the cylindrical body 931. The breakable portion 933 is broken by bending the solid columnar portion 932 together with the short tube 930 with fingers to separate the solid columnar portion 932 from the cylindrical body 931. As a result, the duct of the sealing member 93 is opened.

The cylindrical body 931 is made of hard materials such as hard polyvinyl chloride, polycarbonate, polyester or the like.

Referring to FIG. 2, the upper portion of the solid columnar portion 932 is wedge-shaped. The upper end of the solid columnar portion 932 is widthwise smaller than the outer diameter of the cylindrical body 931 and widthwise larger than the inner diameter of the second tube 91. This is because the solid columnar portion 932 does not seal the second tube 91 after the solid columnar portion 932 is broken and separated from the cylindrical body 931. As shown in FIG. 2, a groove 935 may be formed on the upper end portion 934 of the solid columnar portion 932 to accelerate the flow of blood.

Figure 3:
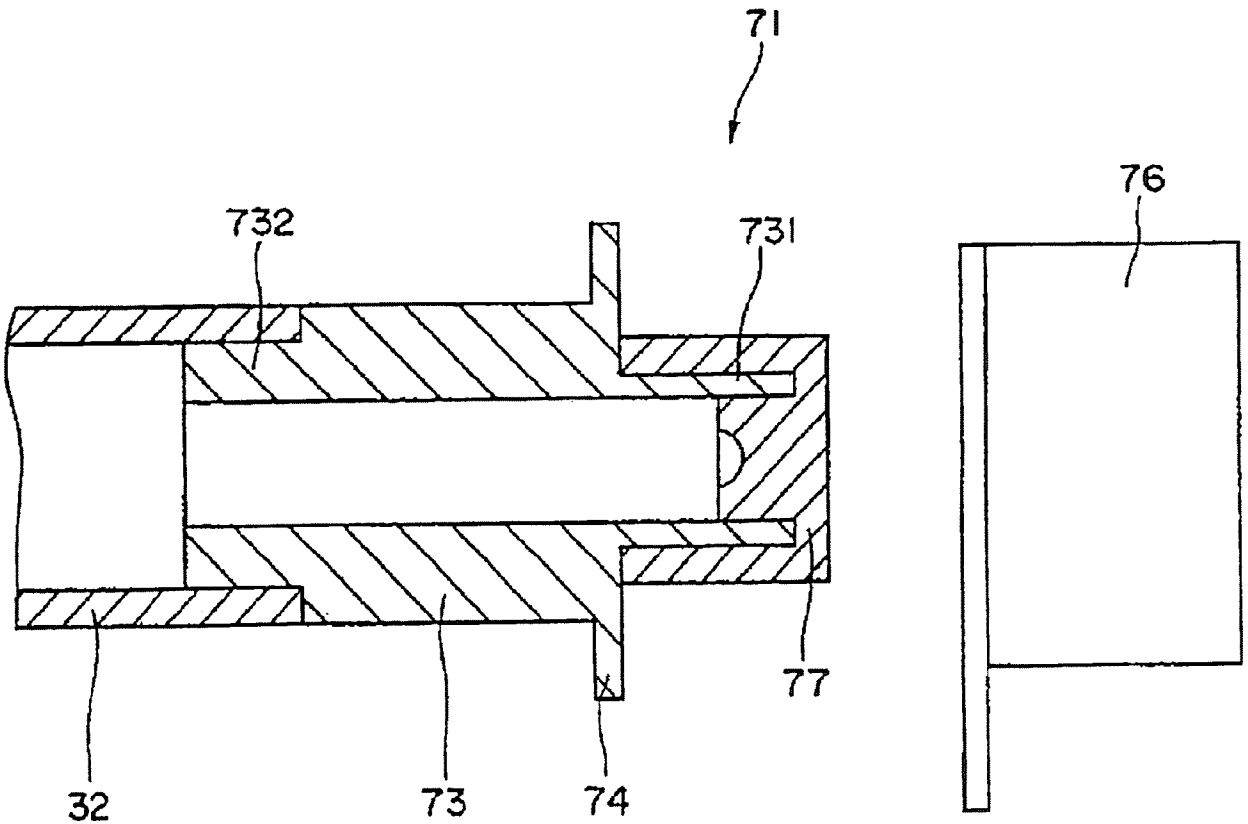
FIG. 3 is a vertical sectional view showing an example of the construction of a sampling port to be used for the blood collecting apparatus of the present invention.

The construction of the sampling port 71 will be described below. FIG. 3 is a vertical sectional view showing an example of the construction of the sampling port 71. In the description made below, the right side of the sampling port 71 in FIG. 3 is referred to as "front side" and the left side thereof is referred to as "rear side".

As shown in FIG. 3, the sampling port 71 comprises a body 73, a plug 77, and a cap 76. The rear side 732 of the body 73 is liquid-tightly connected with the second branch connector 32. The body 73 is substantially cylindrical and has a rib 74 erected from the peripheral surface thereof.

The plug 77 is fitted on a front end 731 of the body 73. The cap 76 to cover the plug 77 is installed on the body 73 at its front side. A blood take-out port is formed at a front portion of the body 73 such that the blood take-out port is proximate to the plug 77.

The body 73 and the rib 74 are made of hard a material such as hard polyvinyl chloride, polycarbonate, polyester or the like.

The material composing the plug 77 is selected from materials into which a blood collecting needle can be pierced comparatively easily. For example, rubber materials such as natural rubber, isoprene rubber, butyl rubber, silicone rubber, urethane rubber, acrylic rubber, and butadiene rubber, styrene-butadiene rubber can be preferably used.

As the material composing the cap 76, rubber materials such as natural rubber, isoprene rubber, butyl rubber, silicone rubber, urethane rubber, acrylic rubber, and butadiene rubber, styrene-butadiene rubber can be preferably used.

Figure 4:
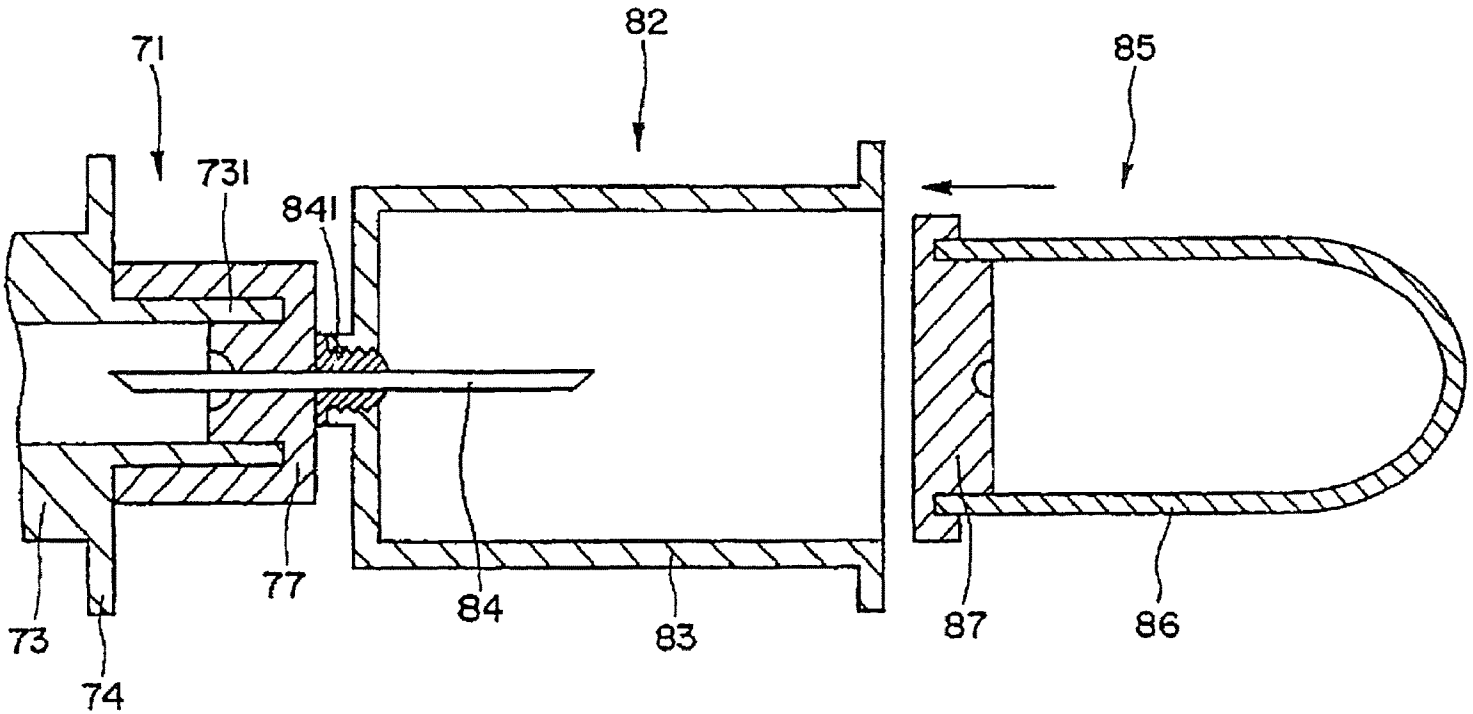
FIG. 4 is a vertical sectional view showing a front end of the sampling port of FIG. 3, a vacuum blood collecting tube and a holder for the blood collecting tube.

As shown in FIG. 4, a holder 82 of the vacuum blood collecting tube (vessel) 85 is connected with the sampling port 71 to allow an initial flow blood or an initial introduced blood (initial flow of collected blood) to be collected by the vacuum blood collecting tube 85 through the holder 82.

The vacuum blood collecting tube 85 comprises a body 86 and a rubber plug 87 fitted on the body 86. The interior of the vacuum blood collecting tube 85 is vacuum or in a pressure-reduced state.

The holder 82 comprises a cylindrical body 83 having a bottom and a double-headed needle 84 provided coaxially with the body 83.

In this case, a member (lure adapter 841) having a male screw formed thereon is fixed to the double-headed needle 84. A female screw engaging the male screw is formed at the center of the bottom portion of the body 83 (left end of body 83 in FIG. 4). The double-headed needle 84 is removably fixed to the body 83 by engaging the male and female screws each other.

The length of the double-headed needle 84 at its left side in FIG. 4 is so set that it can be pierced sufficiently into the plug 77. The length thereof at its right side is also so set that it can be pierced sufficiently into the rubber plug 87.

Although not shown in FIG. 4, it is possible to form an elastic covering member covering the double-headed needle 84 at least one side of the lure adapter 841 to prevent blood from leaking from the double-headed needle 84.

With reference to FIGS. 1 and 4, the operation of the blood collecting apparatus 1, namely, the blood collecting method that is carried out by using the blood collecting apparatus 1 will be described below.

The blood collecting method is carried out by using a blood collecting apparatus 1 comprising a blood collecting needle 152; a blood collecting bag 10 for accommodating collected blood; a first tube 15 whose one end communicates with the blood collecting bag 10 and other end communicates with the blood collecting needle 152; a branch portion 92 provided on a portion of the first tube 15; a second tube 91 connected with the branch portion 92 at one end thereof and having a blood take-out port 71; and a flexible resin bag 20 having a third tube 31 communicating with the second tube.

The blood collecting method comprises the step of piercing a blood collecting needle into a donor when a portion of the first tube positioned between the branch portion and the blood collecting bag is sealed; the step of removing air inside the first and second tubes by introducing an initial flow blood (initial introduced blood) from the donor into a portion of the first tube between the blood collecting needle and the branch portion and into the second tube and by accommodating air inside the portion of the first tube positioned between the blood collecting needle and the branch portion and air inside the second tube in the flexible resin bag; the step of sampling a predetermined amount of blood from the initial flow blood by using the blood take-out port; and the step of collecting a predetermined amount of blood by intercepting communication between the first tube and the flexible resin bag and by communicating the portion of the first tube between the blood collecting needle and the branch portion with a portion of the first tube between the branch portion and the blood collecting bag.

Initially, the step of piercing the blood collecting needle 152 into a donor is performed in the condition that a portion of the first tube (first tube 15b at the side of blood collecting bag 10) positioned between the branch portion (first branch connector 92) and the blood collecting bag 10 is sealed and the first tube 15a is communicated to the flexible resin bag 20.

More specifically, as shown in FIG. 1, the first tube 15 (first tube 15b at the side of blood collecting bag 10) is sealed with the clamp 16 to close (intercept) the duct thereof. The clamp 33 is opened to open the duct of the third tube 31.

Then, the blood collecting needle 152 is pierced into the vein (blood vessel) of the donor. When it is confirmed that the blood collecting needle 152 is in the vein, the hub 151 is fixed with a tape. Then, to open the duct of the sealing member 93, the breakable portion 933 of the sealing member 93 is broken to separate the solid columnar body 932 from the cylindrical body 931.

After completing the needle-piercing step, the step of removing air from the tubes is performed. That is, an initial flow blood from the donor is introduced into the portion of the first tube (first tube 15a at the side of the blood collecting needle 152) between the blood collecting needle 152 and the branch portion (the first branch connector 92) and into the second tube 91 to accommodate the air inside the portion of the first tube (first tube 15a at the side of the blood collecting needle 152) positioned between the blood collecting needle 152 and the branch portion 92 and the air inside the second tube 91 in the flexible resin bag 20.

More specifically, by carrying out the needle-piercing step, the initial flow of the collected blood is introduced into the second tube 91 through the blood collecting needle 152, a part of the first tube 15 (the first tube 15a at the side of the blood collecting needle 152) and the first branch connector 92, thus flowing toward the sampling port 71. In this case, the duct of the first tube 15 is intercepted with the clamp 16. Thus, the blood flows from the first tube 15 (the first tube 15a at the side of the blood collecting needle 152) to the second tube 91 through the first branch connector 92. The blood is introduced into the second tube 91 by utilizing the pressure of the vein and locating the sampling port 71 and the bag 20 below the position at which the blood collecting needle 152 is pierced into the donor.

In introducing the collected blood into the second tube 91, the air inside a part of the first tube 15 (the first tube 15a at the side of the blood collecting needle 152), the air inside the second tube 91, and the air inside the first branch connector 92 flow into the third tube 31 through the second branch connector 32, thus being exhausted from one end of the third tube 31 and collected by the bag 20. In other words, decrease of the volume of the lumen of a part of the first tube 15 (first tube 15a at the side of the blood collecting needle 152) and the second tube 91 caused by the introduction of the blood thereinto, namely, increase in the pressure of the lumen of the first tube 15 and the second tube 91 can be suppressed (restrained) by the expansion of the bag 20. That is, because the pressure inside the first tube 15 and the second tube 91 can be kept substantially constant, it is possible to prevent an excess load from being applied to blood cells. Thus, it is possible to prevent the blood from hemolyzing. Further, it never happens that the blood flows into the first branch connector 92 at the side of the clamp 16.

After the step of removing the air from the tubes is performed, the step of sampling blood from the initial flow blood is performed. That is, the step of sampling a predetermined amount of blood from the blood take-out port (sampling port 71) is performed. In the step of sampling blood, it may be sampled a part of the initial flow blood or blood including all of the initial flow blood.

More specifically, when the blood has reached proximately to the second branch connector 32, the third tube 31 is sealed with the clamp 33 to close (intercept) the duct thereof thereby to stop the introduction of the blood.

Then, as shown in FIGS. 3 and 4, the cap 76 is removed from the body 73 of the sampling port 71. Then, the double-headed needle 84 of the holder 82 is pierced into the plug 77 of the sampling port 71 and penetrated therethrough to install the holder 82 on the sampling port 71.

Then, to sample or collect blood from the initial flow blood, the vacuum blood collecting tube 85 is inserted into the innermost portion of the holder 82 and pressed thereinto, and the double-headed needle 84 of the holder 82 is pierced through the rubber plug 87. As a result, the blood is sucked into the vacuum blood collecting tube 85 and collected thereby. In this case, the interior of the first tube 15 (the first tube 15a at the side of the blood collecting needle 152) and that of the second tube 91 both positioned between the blood collecting needle 152 and the sampling port 71 are mostly filled with the blood. Thus, when the double-headed needle 84 of the holder 82 is pierced through the rubber plug 87 of the vacuum blood collecting tube 85 to suck the blood into the vacuum blood collecting tube 85, an excess load can be prevented from being applied to blood cells. Thus, it is possible to prevent the blood from hemolyzing, and further, it never happens that the blood flows into the first branch connector 92 at the side of the clamp 16.

When the sampling of the initial flow blood into the first vacuum blood collecting tube 85 is completed, the vacuum blood collecting tube 85 is extracted from the holder 82. Then, as necessary, the next vacuum blood collecting tube 85 is inserted through the holder 82 and pressed into the innermost portion of the holder 82. Then, the double-headed needle 84 of the holder 82 is pierced into the rubber plug 87 and penetrated therethrough. As a result, the blood is sucked into the vacuum blood collecting tube 85 and collected thereby. This operation is repeated to collect the initial flow blood into a necessary number of the vacuum blood collecting tubes 85.

After the blood collecting into the vacuum blood collecting tube 85, i.e., after the collecting of the initial flow blood into the vacuum blood collecting tubes 85 terminates, the holder 82 is removed from the sampling port 71, and then, the cap 76 is installed on the body 73 of the sampling port 71.

Because the plug 77 is fitted on the body 73 of the sampling port 71, the plug 77 prevents leak of the blood.

After the step of sampling blood from the initial flow blood terminates, the communication between the first tube 15 and the flexible resin bag 10 is intercepted, the main blood collecting step is performed. That is, a predetermined amount of blood is collected by communicating the first tube 15a with the portion of the first tube (the first tube 15b at the side of the blood collecting bag 10) positioned between the first branch portion 92 and the blood collecting bag 10.

More specifically, the step of collecting the blood into the blood collecting bag 10 is started. The blood collection is performed by using a blood collecting device of decompression type or by locating the blood collecting bag 10 at a position below the position at which the blood collecting needle 152 is pierced into the donor, namely, by utilizing the difference between the levels of the two positions.

In this case, the clamp 16 is opened to open the duct of the first tube 15. Consequently, the blood of the donor flows through the first tube 15, thus being introduced into the blood-accommodating portion 13 of the blood collecting bag 10.

After a predetermined amount of blood is collected, the blood collecting needle 152 is removed from the blood vessel of the donor. Then, the cap 153 is installed on the hub 151. If necessary, the second tube 91 and the first tube 15 are fused, respectively with tube sealer or the like. Then, sealed portions of the first and second tubes 15 and 91 are cut off to remove the portion thereof located at the side of the sampling port 71. In this manner, it is possible to obtain the blood collecting bag 10 accommodating the blood not containing the initial flow blood.

In the case of the above-described bag-connected device, the blood accommodated in the blood collecting bag 10 is centrifuged to separate it into a plurality of blood components such as red blood cells, buffy coat, and blood plasma. Then, the obtained blood components are delivered to a predetermined blood component bag connected with the blood collecting bag 10, according to the normal procedure.

The initial flow blood collected in the vacuum blood collecting tube 85 is discarded or can be used for biochemical examinations of blood serum and examinations of the antibody for virus (for example, AIDS, hepatitis and the like) of infectious disease.

As described above, according to the blood collecting apparatus 1, it is possible to collect not containing an initial part of the initial flow blood having a probability of microbism easily and reliably. Thus, the blood collecting apparatus 1 prevents inclusion of bacteria into collected blood or respective components separated from the collected blood, thus having a high degree of safety.

If the blood collecting apparatus 1 does not have the second branch connector 32, the third tube 31, the clamp 33, and the bag 20, there is a possibility that some of the initial flow blood flows into the first branch connector 92 at the side of the clamp 16 and is left therein. In this case, the blood remaining there may enter into the vacuum blood collecting tube 85 when the main blood collecting is carried out.

The main reason for the penetration of the blood into the first branch connector 92 at the side of the clamp 16 is as follows: Let it be supposed that the blood collecting apparatus 1 does not have the bag 20. In this case, in the collecting of the initial flow blood into the vacuum blood collecting tube 85 by introducing it into the second tube 91, the air inside the first tube 15a and the second tube 91 has nowhere to escape and thus cannot be exhausted to the outside. Thus, the interior of the portion of the first tube 15 and the second tube 91 located between the blood collecting needle 152 and the sampling port 71 cannot be filled with the blood, which causes the interface between the air and the blood is stopped at a portion of the first tube 15 or the second tube 91. When the vacuum blood collecting tube 85 is installed on the holder 82 in this state, the air inside the first tube 15 and the second tube 91 is sucked into the vacuum blood collecting tube 85 immediately after the vacuum blood collecting tube 85 and the sampling port 71 communicate with each other. As a result, the duct of the first tube 15 and that of the second tube 91 become decompressed rapidly. To restore the decompressed state inside the circuit to a normal pressure, the inside of the circuit is filled with the blood. At this time, the blood also flows into the first branch connector 92 at the side of the clamp 16.

Because the blood collecting apparatus 1 has the second branch connector 32, the third tube 31, the clamp 33, and the bag 20, the blood is prevented from being introduced into the first branch connector 92 at the side of the clamp 16, as described above. Thus, it is possible to eliminate the initial flow blood reliably.

If the blood collecting apparatus 1 does not have the second branch connector 32, the third tube 31, the clamp 33, and the bag 20, the blood introduced into the vacuum blood collecting tube 85 may be hemolyzed. The hemolysis may cause sodium and potassium contained in blood serum to be measured at a low accuracy.

The cause of the occurrence of the hemolysis is as follows: As described above, let it be supposed that the blood collecting apparatus 1 does not have the bag 20. In this case, in the collecting of the initial flow blood into the vacuum blood collecting tube 85 by introducing it into the second tube 91, the interior of the portion of the first tube 15 and the second tube 91 located between the blood collecting needle 152 and the sampling port 71 cannot be filled with the blood. When the vacuum blood collecting tube 85 is installed on the holder 82 in this state, the air inside the first tube 15 and the air inside the second tube 91 are sucked into the vacuum blood collecting tube 85 immediately after the vacuum blood collecting tube 85 and the sampling port 71 communicate with each other. As a result, the duct of the first tube 15 and that of the second tube 91 become decompressed rapidly. At this time, the first tube 15 and the second tube 91 are crushed, depending on the position of the blood collecting needle 152, the degree of softness of blood vessel, and the like. As a result, the sectional area of the duct of the first tube 15 and that of the second tube 91 are reduced and negative pressure is comparatively large (sucking-caused moving speed of blood is comparatively large). Consequently, cells and in particular red blood cells of the collected initial flow blood are damaged.

Because the blood collecting apparatus 1 has the second branch connector 32, the third tube 31, the clamp 33, and the bag 20, the blood is prevented from being hemolyzed, as described above.

It is normal to collect the initial flow blood by sequentially providing the holder 82 with a plurality of the vacuum blood collecting tubes 85. If the blood collecting apparatus 1 does not have the second branch connector 32, the third tube 31, the clamp 33, and the bag 20, the first vacuum blood collecting tubes 85 has a smaller amount of the initial flow blood than a predetermined collectable amount (maximum amount of initial flow blood to be collected by sucking in decompressed state). The shortage of the amount of the initial flow blood affects the number of items to be examined, examination accuracy, and workability in examination adversely.

The main reason for the shortage of the amount of the initial flow blood is as follows: Let it be supposed that the blood collecting apparatus 1 does not have the bag 20. In this case, in the collecting of the initial flow blood into the vacuum blood collecting tube 85 by introducing it into the second tube 91, the air inside the first tube 15a and the second tube 91 cannot be exhausted to the outside. Thus, the interior of the portion of the first tube 15 and the second tube 91 located between the blood collecting needle 152 and the sampling port 71 cannot be filled with the blood. When the vacuum blood collecting tube 85 is installed on the holder 82 in this state, the air inside the first tube 15 and the air inside the second tube 91 are sucked into the vacuum blood collecting tube 85 and collected thereby.

The blood collecting apparatus 1 has the second branch connector 32, the third tube 31, the clamp 33, and the bag 20. Thus, as described previously, the initial flow blood can be introduced into the first vacuum blood collecting tube 85, with the interior of the portion of the first tube 15 and the second tube 91 located between the blood collecting needle 152 and the sampling port 71 being filled with blood. Further, when the vacuum blood collecting tube 85 is installed on the holder 82, the third tube 31 is sealed with the clamp 33 to intercept the duct thereof. Therefore, it is possible to prevent the air inside the bag 20 and the air inside the portion of the third tube 31 located between the clamp 33 and the bag 20 from being introduced into the vacuum blood collecting tube 85 and thus allow the amount of the initial flow blood which is introduced into the first vacuum blood collecting tubes 85 to be substantially equal to that the predetermined collectable blood amount.

Further, because the blood collecting apparatus 1 has the sealing member 93 provided on the second tube 91, it is possible to select the time at which a collected initial flow blood starts to flow toward the second tube 91. Thus, according to an instrument to be connected with, installed on or inserted into the sampling port 71, the collected initial flow blood can be flowed through the second tube 91 at an appropriate timing.

Further, the blood collecting apparatus 1 has the sealing member 93 serving as the second duct-sealing member. The sealing member 93 has a higher degree of operability than a clamp and a forceps.

Further, the blood collecting apparatus 1 has the clamp 16 serving as the first duct-sealing member. The clamp 16 has a higher degree of operability than other sealing members.

As described previously, the inner diameter of the second tube 91 is set comparatively small (0.5-2.0 mm), and the thickness thereof is set comparatively large (the outer diameter thereof to 2-4 times as large as the inner diameter thereof) to prevent the second tube 91 from being deformed (crushed) at the time of high pressure-steam sterility.

The second embodiment of the blood collecting apparatus of the present invention will be described below.

The blood collecting apparatus 1a of the second embodiment comprises a blood collecting needle 152 for collecting blood from a donor; a blood collecting bag 10 for accommodating collected blood; a first tube 15 (15a, 15b) whose one end communicates with the blood collecting bag 10 and other end communicates with the blood collecting needle 152; a branch portion 92 provided on a portion of the first tube 15; a second tube 91 connected with the branch portion 92 at one end thereof and having a blood take-out port at the other end thereof; and a filter 41 gas-permeable and blood-unpermeable and communicable with an interior of the second tube 91.

Figure 5:
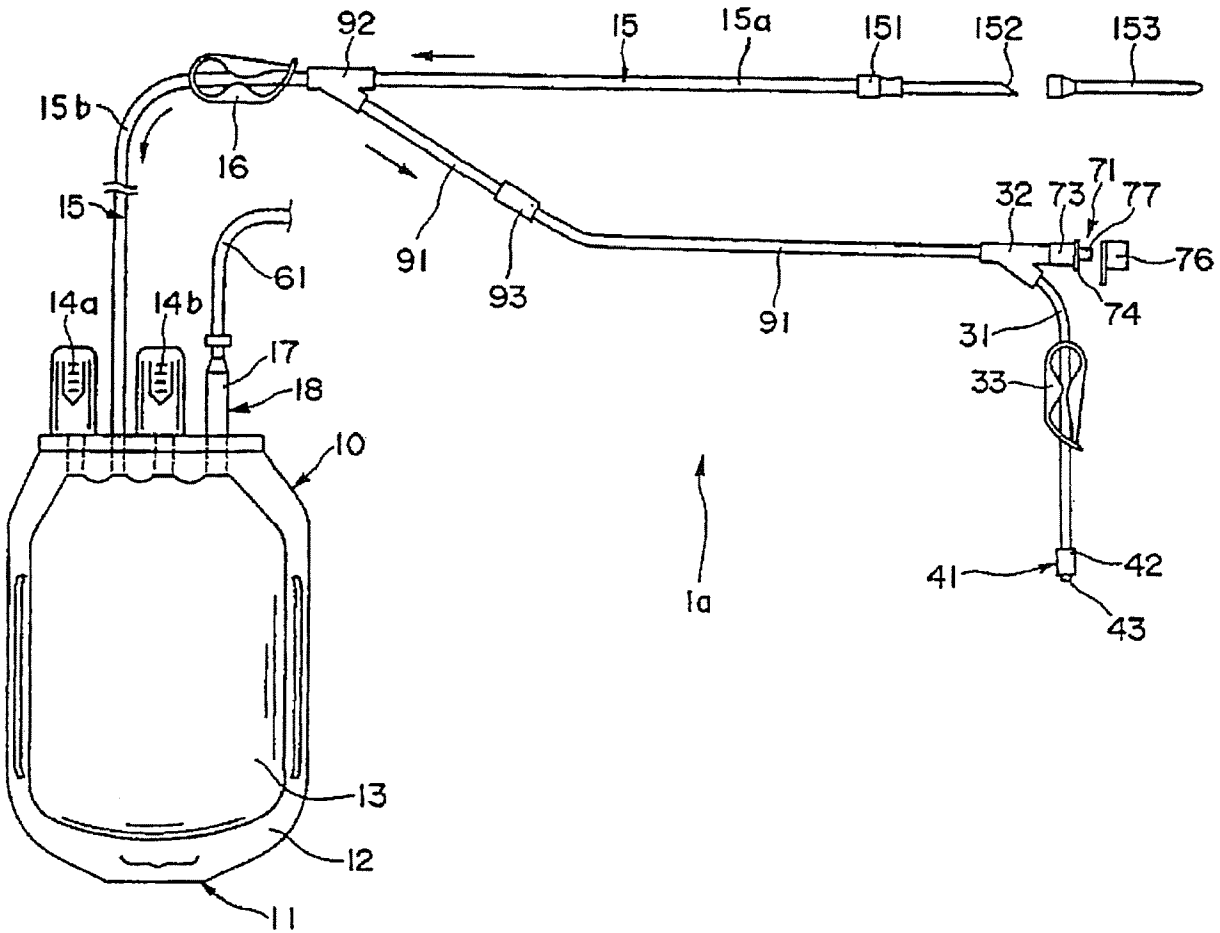
FIG. 5 is a plan view showing a second embodiment of the blood collecting apparatus of the present invention.

FIG. 5 is a plan view showing the second embodiment of the blood collecting apparatus of the present invention. Description of constructions of the blood collecting apparatus of the second embodiment same as those of the blood collecting apparatus of the first embodiment is omitted herein. Thus, only the constructions of the blood collecting apparatus of the second embodiment different from those of the blood collecting apparatus of the first embodiment will be described below.

As shown in FIG. 5, in a blood collecting apparatus 1a, a filter 41 is provided at one end of the third tube 31, instead of the flexible resin bag 20 of the blood collecting apparatus 1. The filter 41 gas-permeable and blood-unpermeable and communicable with the interior of the second tube 91 is capable of exhausting air inside the first tube 15a at the side the blood collecting needle 152 and air inside the second tube 91 when the blood collecting apparatus 1a is used. Other constructions of the blood collecting apparatus 1a are similar to those of the blood collecting apparatus 1.

Figure 6:
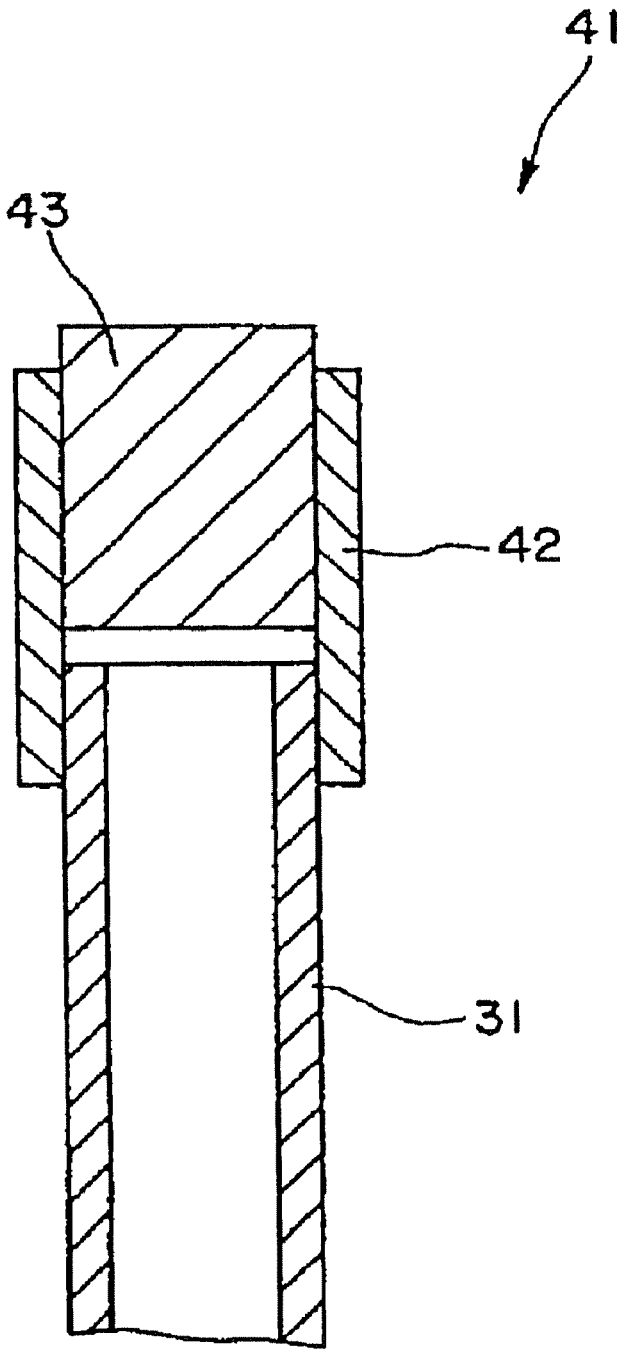
FIG. 6 is a sectional view showing an example of a filter for use in the blood collecting apparatus of the present invention.

FIG. 6 is a sectional view showing an example of the construction of the filter 41 of the blood collecting apparatus 1a.

As shown in FIG. 6, the filter 41 comprises a tubular body 42 and a cylindrical filter member 43 gas-permeable (ventilative) and blood-unpermeable. An end of the third tube 31 is liquid-tightly connected with the lower side of the tubular body 42 in FIG. 6. The filter member 43 is fitted into an upper portion of the tubular body 42 in FIG. 6. The tubular body 42 is made of a hard material such as polycarbonate or the like. The filter member 43 can be made of a sintered material containing polyethylene, polypropylene or polyimide as its main component.

The operation (blood collecting method using the blood collecting apparatus) of the blood collecting apparatus 1a is similar to that of the blood collecting apparatus 1 except that in the blood collecting apparatus 1a, air is exhausted to the outside through the body 43 of the filter 41. The effect of the blood collecting apparatus 1a is also similar to that of the blood collecting apparatus 1.

With reference to FIG. 5, the operation of the blood collecting apparatus 1a, namely, the blood collecting method to be carried out by using the blood collecting apparatus 1a will be described below.

The second blood collecting method is carried out by using a blood collecting apparatus 1a comprising a blood collecting needle 152 for collecting blood from a donor; a blood collecting bag 10 for accommodating collected blood; a first tube 15 whose one end communicates with the blood collecting bag 10 and other end communicates with the blood collecting needle 152; a branch portion 92 provided on a portion of the first tube 15; a second tube 91 connected with the branch portion 92 at one end thereof and having a blood take-out port 71; and a filter 41 gas-permeable and blood-unpermeable and communicable with an interior of the second tube.

The second blood collecting method comprises the steps of piercing a blood collecting needle into a donor when a portion of the first tube positioned between the branch portion and the blood collecting bag is sealed; exhausting air inside the first and second tubes from the filter by introducing an initial flow blood from the donor into a portion of the first tube between the blood collecting needle and the branch portion and into the second; sampling blood from the initial flow blood by using the blood take-out port; and collecting a predetermined amount of blood by intercepting communication between the first tube and the filter and by communicating the portion of the first tube between the blood collecting needle and the branch portion with a portion of the first tube between the branch portion and the blood collecting bag.

The blood collecting needle-piercing step of the second embodiment is the same as that of the first embodiment More specifically, as shown in FIG. 5, the first tube 15 (the first tube 15b at the side of the blood collecting bag 10) is sealed with the clamp 16 to close (intercept) the duct thereof. The clamp 33 is opened to open the duct of the third tube 31.

Then, the blood collecting needle 152 is pierced into the vein (blood vessel) of a donor. When it is confirmed that the blood collecting needle 152 is in the vein, the hub 151 is fixed with a tape. Then, to open the duct of the sealing member 93, the breakable portion 933 of the sealing member 93 is broken to separate the solid columnar body 932 from the cylindrical body 931.

After completing the needle-piercing step, the step of removing the air from the tubes is performed. That is, the blood (initial flow blood) of the donor is introduced into the portion of the first tube 15a and into the second tube 91 to exhaust air inside the first tube 15a and air inside the second tube 91 from the filter 41.

More specifically, the blood of the donor is introduced into the first tube (the first tube 15a at the side of the blood collecting needle) between the blood collecting needle 152 and the branch portion (first branch connector 92) and into the second tube 91 to exhaust the air inside the first tube (the first tube 15a at the side of the blood collecting needle 152) positioned between the blood collecting needle 152 and the branch portion 92 and the air inside the second tube 91 to the outside from the filter 41.

More specifically, by carrying out the needle-piercing step, the initial flow blood is introduced into the second tube 91 through the blood collecting needle 152, a part of the first tube 15 (the first tube 15a at the side of the blood collecting needle 152) and the first branch connector 92, thus flowing toward the sampling port 71. In this case, the duct of the first tube 15 is intercepted with the clamp 16. Thus, the blood flows from the first tube 15 (the first tube 15a at the side of the blood collecting needle 152) to the second tube 91 through the first branch connector 92. The blood is introduced into the second tube 91 by utilizing the pressure of the vein and locating the sampling port 71 below the position at which the blood collecting needle 152 is pierced into the donor.

In introducing the initial flow blood into the second tube 91, the air inside a part of the first tube 15 (the first tube 15a at the side of the blood collecting needle), the second tube 91, and the first branch connector 92 flow into the third tube 31 through the second branch connector 32, thus being exhausted from the filter 41 positioned at the termination of the third tube. That is, because the air inside a part of the first tube 15 (the first tube 15a at the side of the blood collecting needle) and the air inside the second tube 91 are exhausted by the introduction of the blood thereinto, the pressure of the lumen of the first tube 15 and the second tube 91 do not increase. That is, because the pressure inside the first tube 15 and the second tube 91 can be kept substantially constant, it is possible to prevent an excess load from being applied to blood cells. Thus, it is possible to prevent the blood from hemolyzing. Further, it does not happen that the blood flows into the first branch connector 92 at the side of the clamp 16.

After the step of removing the air from the tubes is performed, step of sampling blood from the initial flow blood is performed. That is, the step of collecting a predetermined amount of blood from the blood take-out port (sampling port 71) is performed. In the step of sampling blood, it may be sampled a part of the initial flow blood or blood including all of the initial flow blood.

More specifically, when the blood has reached proximately to the second branch connector 32, the third tube 31 is sealed with the clamp 33 to close (intercept) the duct thereof thereby to stop the introduction of the blood.

Then, the cap 76 is removed from the body 73 of the sampling port 71. Then, the double-headed needle 84 of the holder 82 is pierced into the plug 77 of the sampling port 71 and penetrated therethrough to install the holder 82 on the sampling port 71.

Then, to collect an initial flow blood, the vacuum blood collecting tube 85 is inserted into the innermost portion of the holder 82 and pressed thereinto, and the double-headed needle 84 of the holder 82 is pierced through the rubber plug 87. As a result, the blood is sucked into the vacuum blood collecting tube 85 and collected thereby. In this case, the interior of the first tube 15 (the first tube 15a at the side of the blood collecting needle 152) and that of the second tube 91 both positioned between the blood collecting needle 152 and the sampling port 71 are mostly filled with the blood. Thus, when the double-headed needle 84 of the holder 82 is pierced through the rubber plug 87 of the vacuum blood collecting tube 85 to suck the blood into the vacuum blood collecting tube 85, an excess load can be prevented from being applied to blood cells. Thus, it is possible to prevent the blood from hemolyzing, and further, it never happens that the blood flows into the first branch connector 92 at the side of the clamp 16.

When the collecting of the initial flow blood into the first vacuum blood collecting tube 85 is completed, the vacuum blood collecting tube 85 is extracted from the holder 82. Then, as necessary, the next vacuum blood collecting tube 85 is inserted through the holder 82 and pressed into the innermost portion of the holder 82. Then, the double-headed needle 84 of the holder 82 is pierced into the rubber plug 87 and penetrated therethrough. As a result, the blood is sucked into the vacuum blood collecting tube 85 and collected thereby. This operation is repeated to collect the initial flow blood is introduced into a necessary number of the vacuum blood collecting tubes 85.

After the blood sampling into the vacuum blood collecting tube 85, i.e., after the collecting of the initial flow bloods into the vacuum blood collecting tubes 85 terminates, the holder 82 is removed from the sampling port 71, and then, the cap 76 is installed on the body 73 of the sampling port 71.

Because the plug 77 is fitted on the body 73 of the sampling port 71, the plug 77 prevents leak of the blood.

After the step of sampling blood from the initial flow blood terminates, the communication between the first tube 15 and the blood flexible resin bag 20 is intercepted and the blood collecting step is performed. That is, a predetermined amount of blood is collected by communicating the first tube 15a with the portion of the first tube (the first tube 15b at the side of the blood collecting bag 10) positioned between the branch portion and the blood collecting bag 10.

More specifically, a main blood collecting into the blood collecting bag 10 is started. The blood collecting is performed by using a blood collecting device of decompression type or by locating the blood collecting bag 10 at a position below the position at which the blood collecting needle 152 is pierced into the donor, namely, by utilizing the difference between the levels of the two positions.

In this case, the clamp 16 is opened to open the duct of the first tube 15. Consequently, the blood of the donor flows through the first tube 15, thus being introduced into the blood-accommodating portion 13 of the blood collecting bag 10.

After a predetermined amount of blood is collected, the blood collecting needle 152 is removed from the blood vessel of the donor. Then, the cap 153 is installed on the hub 151. If necessary, the second tube 91 and the first tube 15 are fused, respectively with tube sealer or the like. Then, sealed portions of the first and second tubes 15 and 91 are cut off to remove the portion thereof located at the side of the sampling port 71.

In this manner, it is possible to obtain the blood collecting bag 10 accommodating the blood not containing the initial flow blood.

The third embodiment of the blood collecting apparatus of the present invention will be described below.

Figure 7:
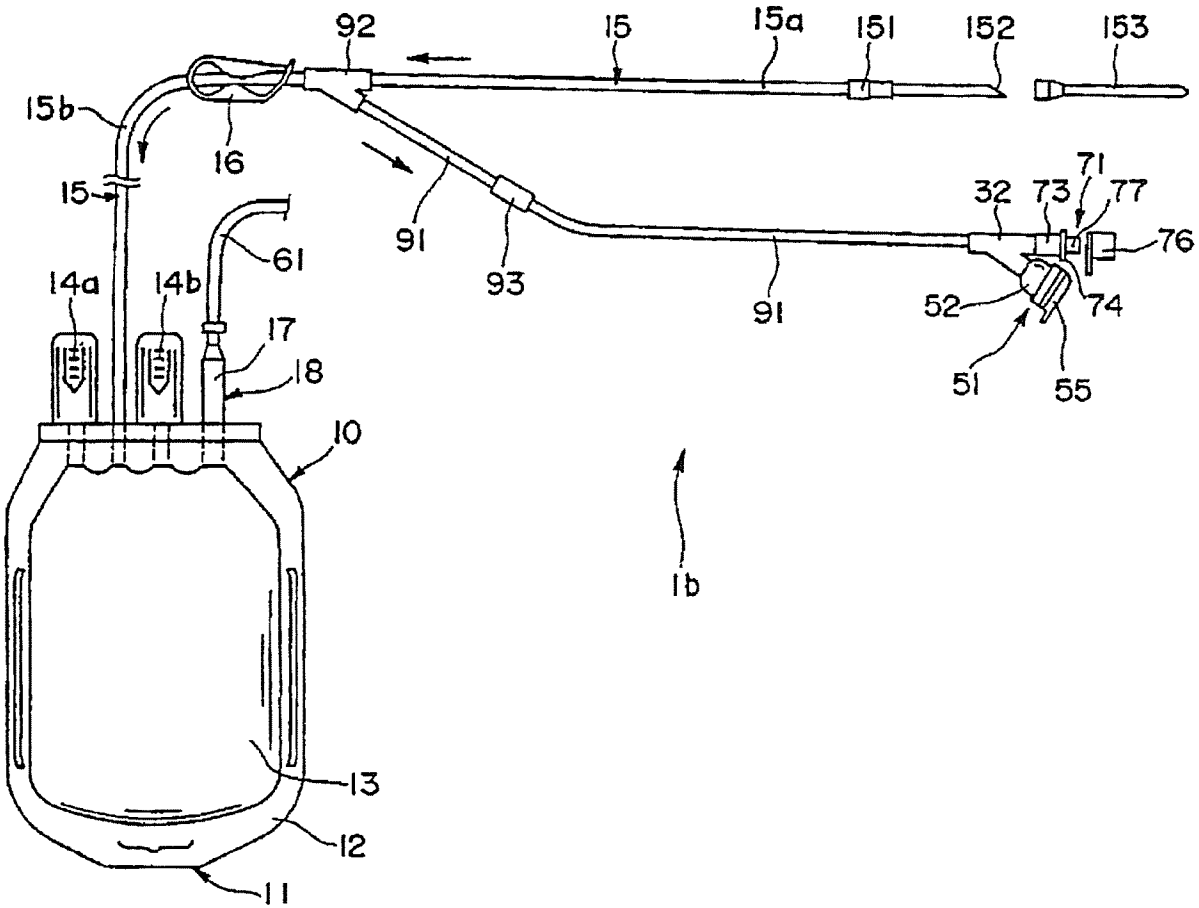
FIG. 7 is a plan view showing a third embodiment of the blood collecting apparatus of the present invention.

FIG. 7 is a plan view showing the third embodiment of the blood collecting apparatus of the present invention. Description of constructions of the blood collecting apparatus of the third embodiment same as those of the blood collecting apparatus of the first embodiment is omitted herein. Thus, only the constructions of the blood collecting apparatus of the third embodiment different from those of the blood collecting apparatus of the first embodiment will be described below.

As shown in FIG. 7, the blood collecting apparatus 1b has a filter provided on the branch connector 32 and a sealable air vent 51 provided thereon. The blood collecting apparatus 1b does not have the third tube 31, the clamp 33, and the flexible resin bag 20 unlike the blood collecting apparatus 1 of the first embodiment. The other constructions of the blood collecting apparatus 1b of the third embodiment are similar to those of the blood collecting apparatus 1 of the first embodiment.

Figure 8:
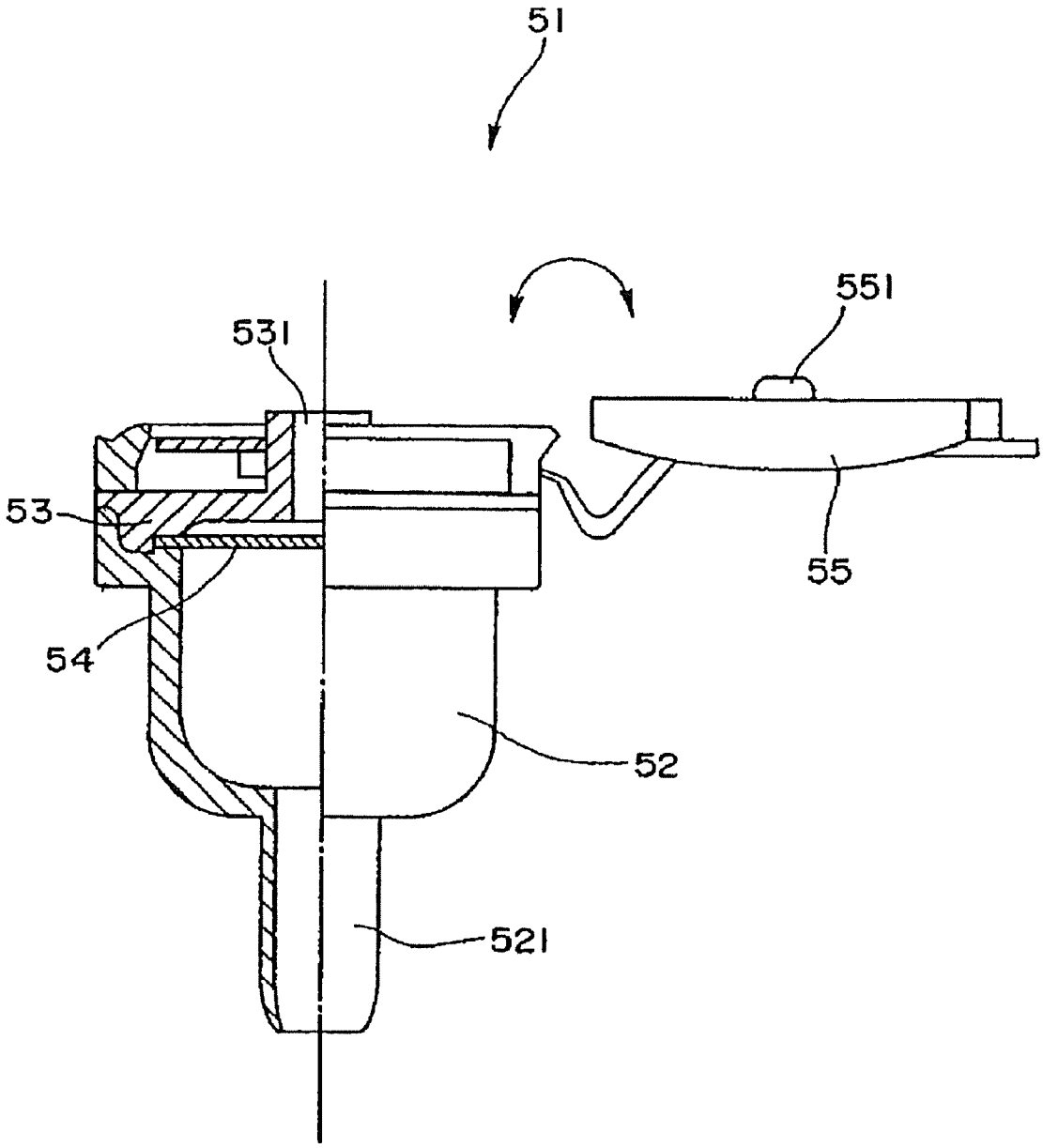
FIG. 8 is a sectional view showing an example of a filter for use in the blood collecting apparatus of the present invention.

FIG. 8 is a sectional view showing an example of the sealable air vent 51 for use in the blood collecting apparatus 1b of the present invention.

As shown in FIG. 8, the air vent (filter) 51 comprises a vent adapter 52, an adapter cap 53, a vent filter (filter body) 54 gas-permeable (ventilative) and blood-unpermeable, and a vent cap 55.

The vent adapter 52 is cylindrical and has a projection 521 formed on a rotational shaft of the cylinder. The projection 521 is pressed into the second branch connector 32.

The disk-shaped vent filter 54 is provided on the upper surface of the vent adapter 52 at the side (upper side in FIG. 8) not provided with the projection 521 such that the vent filter 54 seals the vent adapter 52. The adapter cap 53 is installed on the periphery of the vent filter 54.

The adapter cap 53 is disk-shaped and has an air-permeable hole 531 at its center to allow air to pass between the inner space of the second branch connector 32 and the outside through the vent filter 54.

A projection 551 which engages the hole 531 when the vent cap 55 is installed on the vent adapter 52 is formed at the center of the vent cap 55. When the projection 551 engages the hole 531, a third duct (duct communicating with the inside of the second tube and the outside through the air vent 51) is intercepted.

That is, when the vent cap 55 is installed on the vent adapter 52 (the vent cap 55 is closed), the third duct is intercepted. When the vent cap 55 is removed from the vent adapter 52 (the vent cap 55 is opened), the third duct is opened. The third duct is constituted of a hollow portion (duct) between the branch point of the second branch connector 32 and a position immediately prior to the vent cap 55 of the air vent 51. The vent cap 55 constitutes a third duct-sealing member. The air vent (filter) 51 constitutes a main portion of the pressure buffering means.

As the vent filter 54, it is possible to used various kinds of membrane filters such as a membrane filter consisting of a polyester resin coated with polyvinyl chloride, a membrane filter consisting of polytetrafluoroethylene laminated on or coating nonwoven cloth of polyethylene, a membrane filter consisting an acetate film coated with silicone resin, and the like.

The operation (blood collecting method using the blood collecting apparatus) of the blood collecting apparatus 1b is similar to that of the blood collecting apparatus 1a except that in the blood collecting apparatus 1b, the or vent cap 55 of the air vent (filter) 51 is opened and closed in the blood collecting apparatus 1b whereas in the blood collecting apparatus 1a, the clamp 33 of the blood collecting apparatus 1a is opened and closed and that in the blood collecting apparatus 1b, air is exhausted to the outside through the vent filter 54 of the air vent The effect of the blood collecting apparatus 1b is also similar to that of the blood collecting apparatus 1.

Figure 9:
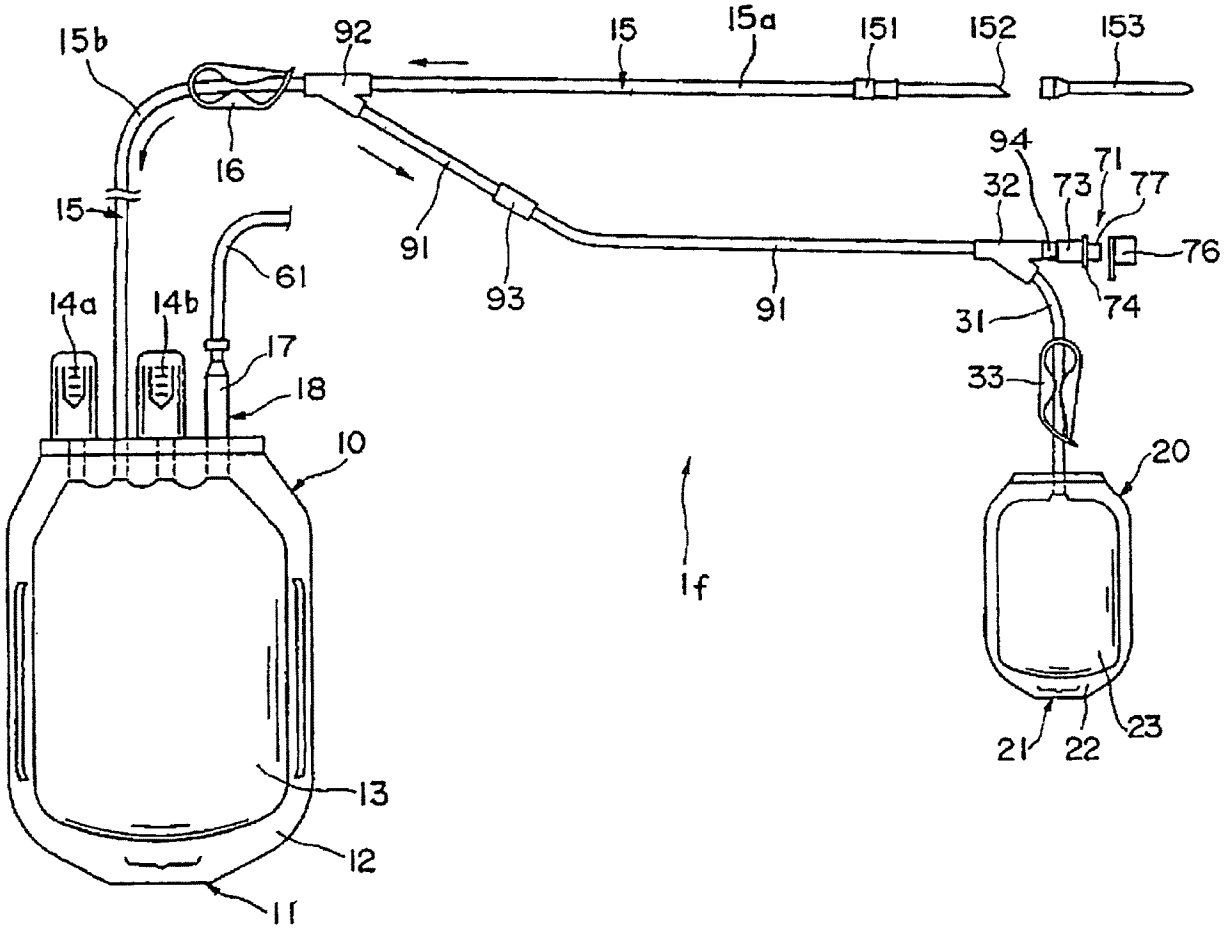
FIG. 9 is a plan view showing a fourth embodiment of the blood collecting apparatus of the present invention.

The blood collecting apparatus of the present invention and the blood collecting methods thereof using each blood collecting apparatus have been described with reference to the drawings. The present invention is not limited to the embodiments, but the construction of each part of the blood collecting apparatus of each embodiment can be replaced with a part having a desired construction provided that it has the same function as that of each part of the blood collecting apparatus of each embodiment For example, as shown in FIG. 9 showing a blood collecting apparatus 1f of the fourth embodiment, the second duct may be provided with a check valve 94 (reverse flow prevention member).

Figure 10:
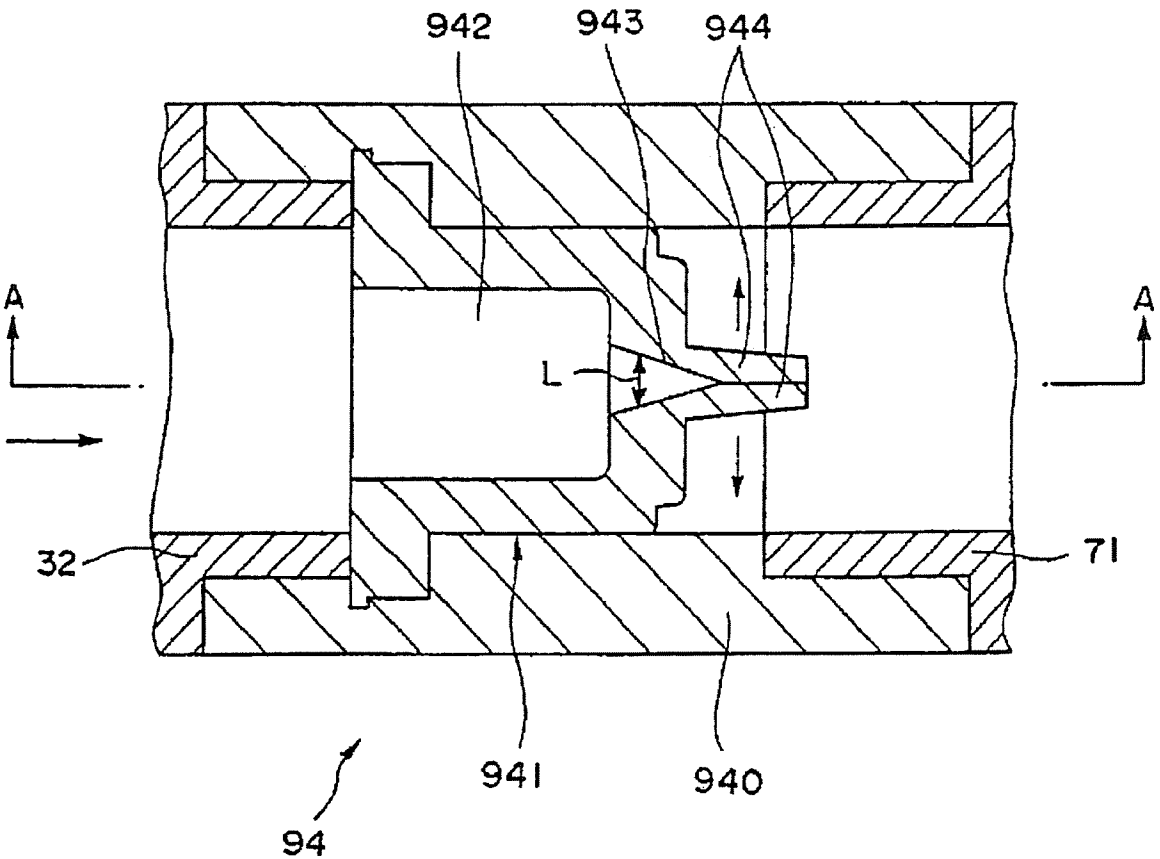
FIG. 10 is a vertical sectional view showing an example of a check valve for use in the blood collecting apparatus of the present invention.
Figure 11:
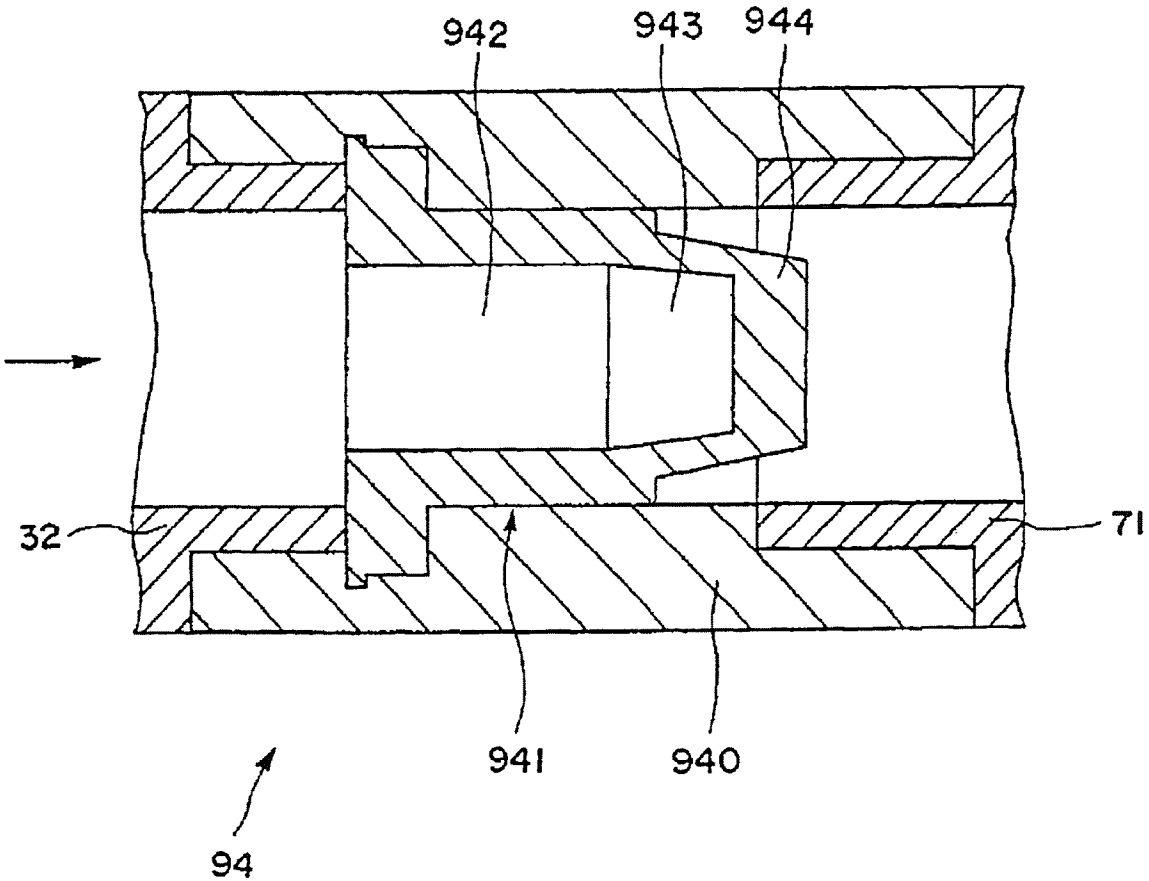
FIG. 11 is a sectional view taken along a line A-A of FIG. 10.

FIG. 10 is a vertical sectional view showing an example of the construction of the check valve 94. FIG. 11 is a sectional view taken along a line A-A of FIG. 10. In the description made below, the right side in FIGS. 10 and 11 is referred to as "front side" and the left side therein is referred to as "rear side".

As shown in FIGS. 10 and 11, the check valve 94 includes a short tube 940 composed of a flexible resin such as soft polyvinyl chloride and a body 941 made of an elastic material. The body 941 is liquid-tightly inserted into the short tube 940 and fixed thereto.

The front end of the short tube 940 is liquid-tightly connected with the sampling port 71. The rear end of the short tube 940 is liquid-tightly connected with the second branch connector 32.

The body 941 has a hollow portion 942 communicating with the second branch connector 32 and forming a part of the blood duct of the check valve 94. A tapered surface 943 is formed on the front end of the hollow portion 942. That is, the vertical length (L) of the front side of the hollow portion 942 decreases gradually from the rear side toward the front side.

A pair of plate-shaped opening/closing members 944 and 944 is formed at the front end of the body 941. The opening/closing members 944 and 944 are in close contact with each other owing to their elastic and restoring forces, thus closing the duct of the check valve 94. When blood flows from the front side to the rear side, the pressure of the blood is applied to the peripheral surface of the opening/closing members 944 and 944, thus acting to bring them into contact each other closely. Thus, the blood does not flow from the front side to the rear side.

When blood flows from the rear side to the front side, a predetermined pressure of the blood is applied to the front end of the tapered surface 943, thus acting to move the opening/closing members 944 and 944 away from each other. As a result, the duct of the check valve 94 is opened, thus flowing the blood from the rear side to the front side.

As the material composing the body 941, rubber materials such as natural rubber, isoprene rubber, butyl rubber, silicone rubber, urethane rubber, acrylic rubber, and butadiene rubber, styrene-butadiene rubber can be preferably used.

The check valve 94 prevents a reverse flow blood. That is, the blood does not flow from the sampling port 71 toward the first branch connector 92, but from the first branch connector 92 toward the sampling port 71.

In the present invention, the position of the check valve 94 is not limited to a specified position as long as it is positioned on the second duct. As described above, it is favorable that the check valve 94 is positioned at the side of the sampling port 71 with respect to the second branch connector 32. It is more favorable that the check valve 94 is positioned between the second branch connector 32 and the sampling port 71.

When the check valve 94 is installed at the above-described position, the check valve 94 does not constitute a pressure drag when blood is flowed to a position proximate to the second branch connector 32. Thus, the check valve 94 allows the introduction of the blood to the bag 20 to be accomplished smoothly.

Figure 12:
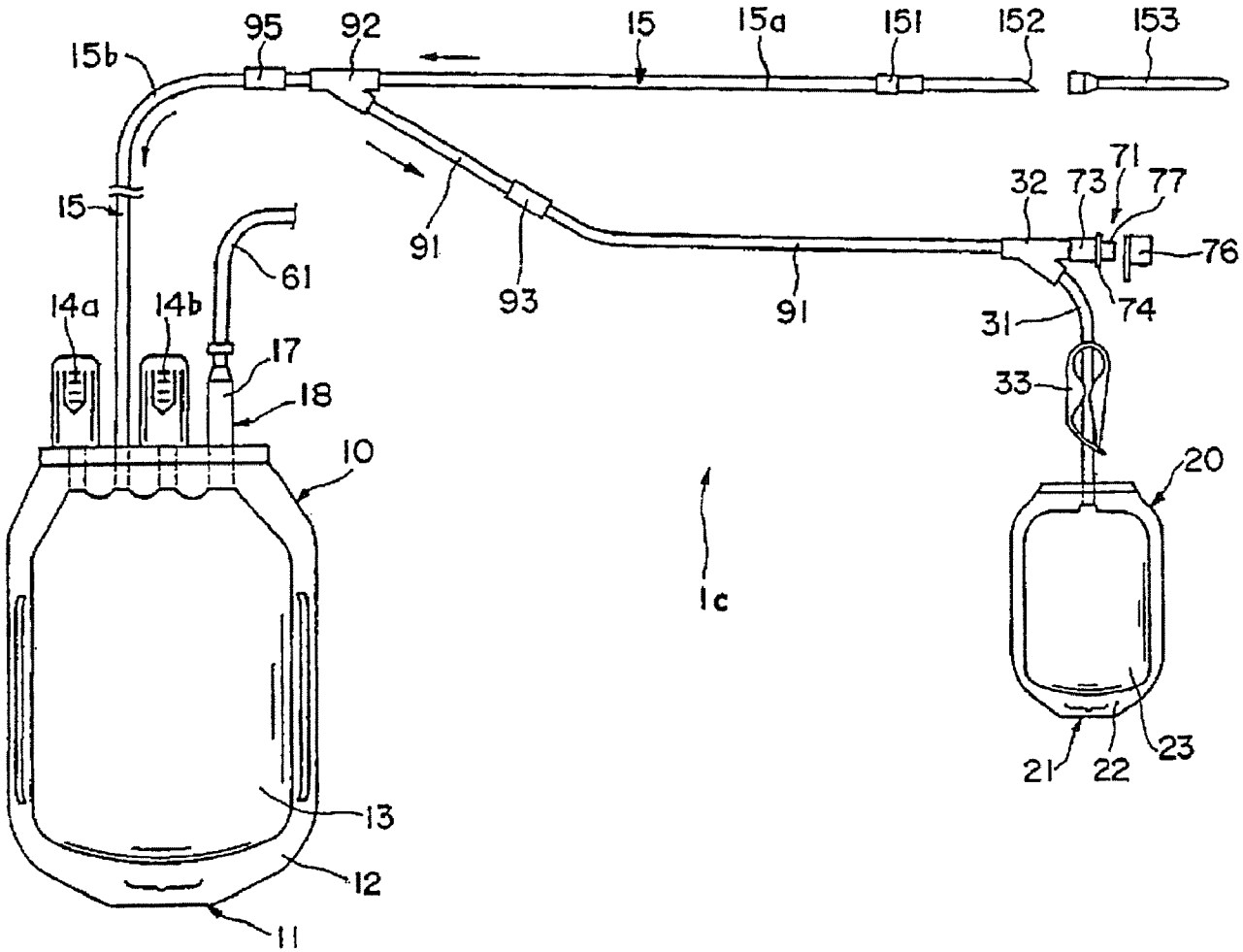
FIG. 12 is a plan view showing the fifth embodiment of the blood collecting apparatus of the present invention.
Figure 13:
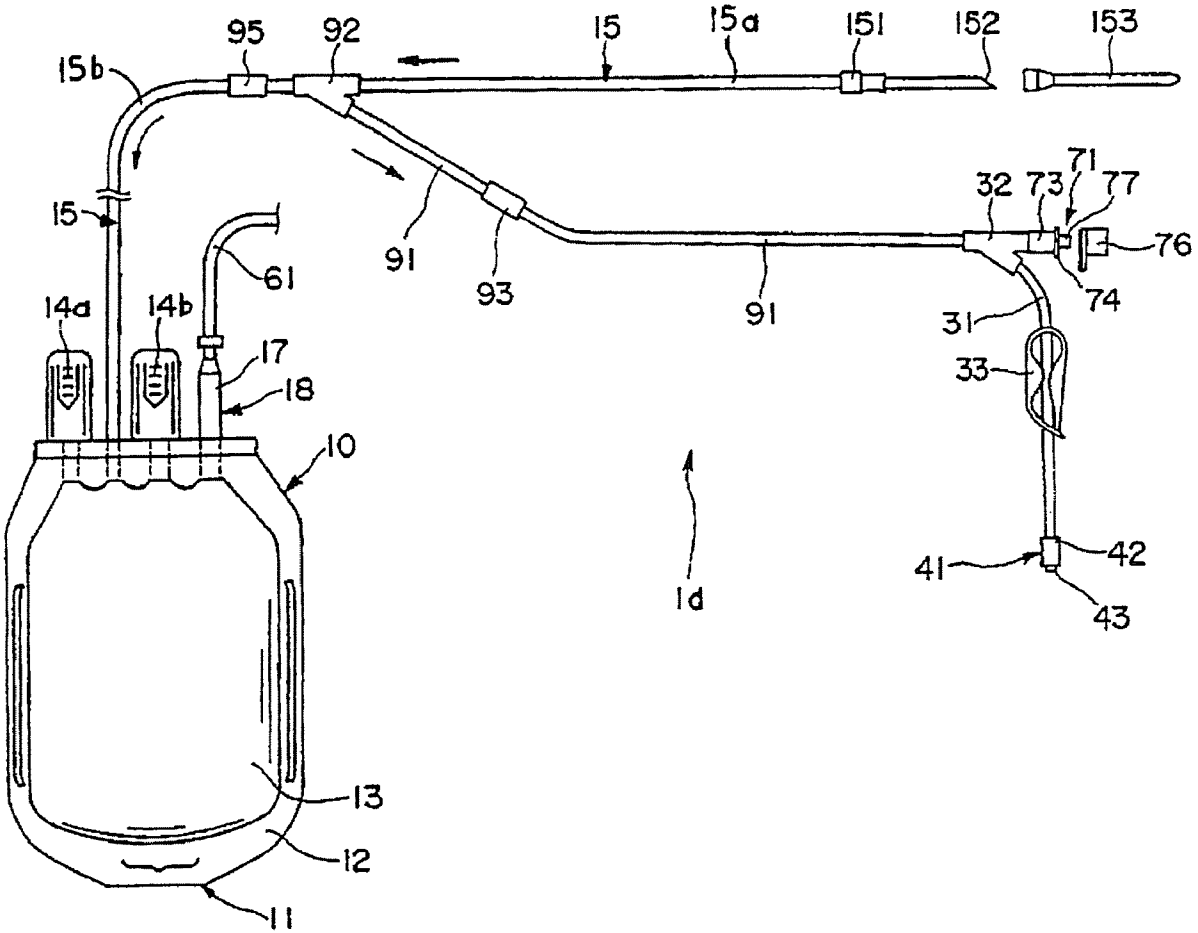
FIG. 13 is a plan view showing a sixth embodiment of the blood collecting apparatus of the present invention.
Figure 14:
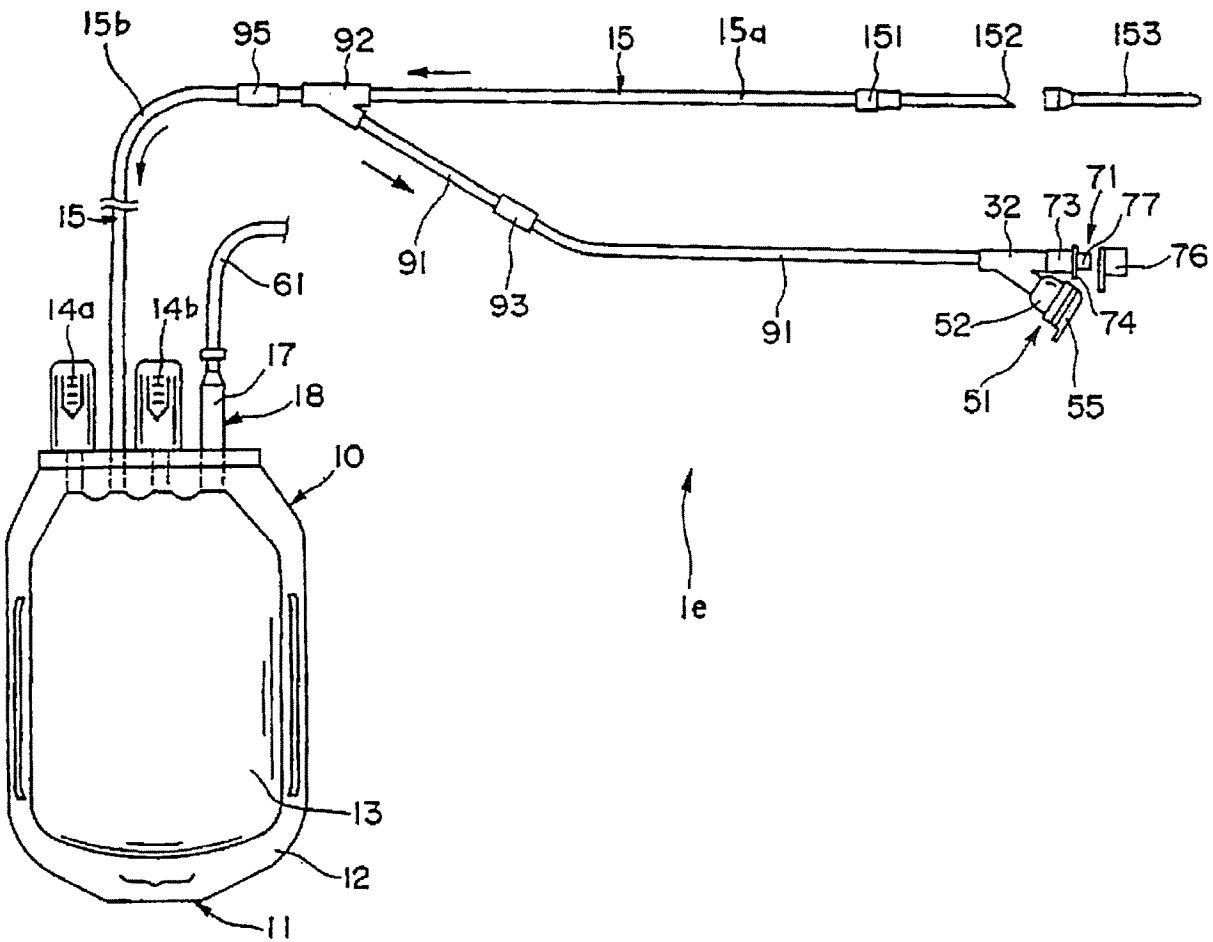
FIG. 14 is a plan view showing a seventh embodiment of the blood collecting apparatus of the present invention.

As shown in FIGS. 12, 13, and 14, the first duct-sealing member may be composed of a sealing member 95 which can be broken to open the first duct That is, the clamp 16 shown in FIGS. 1, 5, and 7 may be replaced with the sealing member 95. As the sealing member 95 of the blood collecting apparatus 1c, 1d, and 1e, a member similar to the above-described sealing member 93 can be used.

In the present invention, the second tube 91 may be closed with a tube-closing member such as a clamp to intercept the duct (second duct). In this case, it is preferable that the tube-closing member is positioned between the first branch connector 92 and the sealing member 93.

It is possible that the second tube 91 is not provided with the sealing member 93 when the second tube 91 is provided with the tube-closing member.

In the present invention, in the construction shown in FIGS. 1 and 5, it is possible to connect the sampling port 71 and the third tube 31 to the end of each branch of the second branch connector 32 reversely. That is, the third tube 31 may be connected with the end of the upper branch of the second branch connector 32 in FIGS. 1 and 5 and the sampling port 71 may be connected with the end of the lower branch thereof in FIGS. 1 and 5.

In the present invention, in the construction shown in FIG. 7, it is possible to connect the sampling port 71 and the air vent 51 to the end of each branch of the second branch connector 32 reversely. That is, the air vent 51 may be connected with the end of the upper branch of the second branch connector 32 in FIG. 7 and the sampling port 71 may be connected with the end of the lower branch thereof in FIG. 7.

In the present invention, the branch portions may be composed of a multi-plug such as a three-way plug instead of the branch connectors as shown in the drawings.

As described above, according to the blood collecting apparatus of the present invention and the blood collecting method thereof, air inside the first tube 15 (first tube 15a at the side of the blood collecting needle 152) between the branch portion 92 and the blood collecting needle 152 and air inside the second tube 91 can be accommodated in the flexible resin or exhausted to the outside. Thus, an initial flow blood is prevented from being left in the branch portion between the first tube and the second tube at the side of the blood collecting bag. That is, it is possible to collect blood not containing a initial part of the initial flow blood having a probability of microbism easily and reliably from blood collected from a donor. Thus, it is possible to prevent inclusion of bacteria into the collected blood or respective components separated from the collected blood, thus having a high degree of safety.

As described above, because the blood collecting apparatus of the present invention has the pressure buffering means for restraining fluctuation of the pressure in the second duct, the initial flow blood is prevented from being left in the branch portion between the first tube and the second tube at the side of the blood collecting bag. That is, it is possible to remove the initial flow blood having a probability of microbism easily and reliably from blood collected from a donor. Therefore, it is possible to prevent inclusion of bacteria into the collected blood or respective components separated from the collected blood, thus having a high degree of safety.

When the initial flow blood is collected (when to be examined is collected), the pressure buffering means prevents (prevents cells in blood from being damaged, for example, hemolysis) an excess load from being applied to the blood, thus allowing the initial flow blood to be collected in a preferable state and preventing a collecting amount of the initial flow blood from being reduced.

Other embodiments of the blood collecting apparatus of the present invention will be described below with reference to the drawings.

Figure 15:
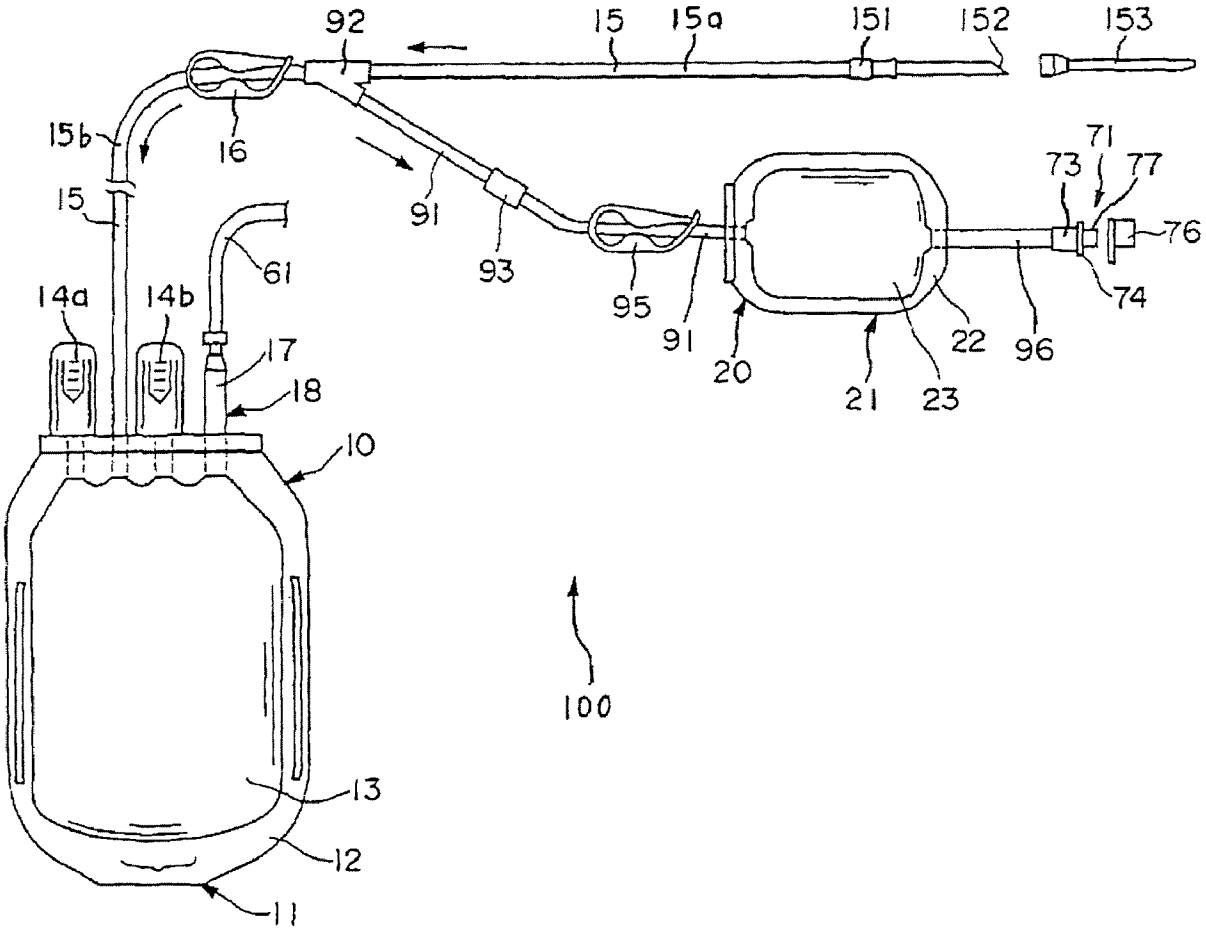
FIG. 15 is a plan view showing an eighth embodiment of the blood collecting apparatus of the present invention.

FIG. 15 is a plan view showing the eighth embodiment of the blood collecting apparatus of the present invention.

Each of blood collecting apparatuses 100, 110, 120, and 130 of the present invention includes a blood collecting needle 152 for collecting blood from a donor; a blood collecting bag 10 for accommodating collected blood; a first duct 15 whose one end communicates with the blood collecting bag 10 and other end communicates with the blood collecting needle 152 to introduce the collected blood into the blood collecting bag 10; a second duct 91 branching from the first duct 15 through a branch portion 92 and having a blood take-out port 73. The second duct 91 has an accommodating portion 20 for accommodating the collected blood temporarily. In other words, each of the blood collecting apparatuses 100, 110, 120, and 130 has the blood accommodating portion 20 provided to the second duct 91 at a portion between the branch portion 92 and the blood take-out port 73.

The blood collecting bag 10 has a body 11 formed by fusing (heat fusion, high frequency fusion or the like) or bonding to each other the periphery of a sealing portion 12 of two sheet materials made of a flexible soft resin such as polyvinyl chloride and laminated on each other, as will be described later.

A blood-accommodating portion 13 accommodating collected blood is formed at an inner portion surrounded with the sealing portion 12 of the body 11. The blood collecting bag 10 may be used as a red blood cell bag for preserving red blood cells. In this case, the blood-accommodating portion 13 accommodates and stores red blood cell rich liquid.

Two openings 14a and 14b each sealed with a peel tab are formed at an upper portion of the body 11 such that they can be opened. An outlet port 18 is formed alongside of the opening 14b. The outlet port 18 is connected with one end of a tube 61 through a sealing member (in other words, connection member) 17. As the sealing member 17, it is possible to use a member having a construction similar to that of a sealing member 93 that will be described later.

Although not shown in FIG. 15, one or more bags such as a blood plasma bag, a buffy coat bag, a platelet bag (in other words, additive solution bag) may be provided at the other end of the tube 61. That is, the blood collecting apparatus 100, 110, 120 and 130 may constitute a bag-connected device.

In the blood collecting apparatus of the present invention, it is possible to omit the provision of the sealing member 17, the outlet port 18, and the tube 61.

One end of the flexible tube 15 communicating with the blood-accommodating portion 13 is connected with the body 11 at an upper portion thereof. The blood collecting needle 152 is installed at the other end of the tube 15 through a hub 151. A cap 153 which is to cover the blood collecting needle 152 is installed on the hub 151. A main part of the first duct is composed of the lumen of the tube 15.

The branch connector (in other words, branch portion) 92 branching bifurcately is provided at a portion of the tube 15. One end of the flexible tube 91 is connected with the branch connector 92. Although the branch connector 92 shown in FIG. 1 consists of a y-shaped tube, the branch connector 92 of the present invention may be Y-shaped, T-shaped or inverse y-shaped. A clamp (in other words, first duct-sealing member or first clamping member) 16 is provided on a portion of the tube 15 between the branch connector 92 and the blood collecting bag 10. Preferably, the clamp 16 is positioned proximately to the branch connector 92.

The blood collecting apparatus 100 has the bag 20 temporarily accommodating the collected blood. The flexible resin bag 20 has the body 21 formed by fusing (heat fusion, high frequency fusion or the like) or bonding to each other the periphery of a sealing portion 22 of two laminated sheet materials made of a flexible soft resin such as polyvinyl chloride, as will be described later. The body 21 has an accommodating portion 23 formed in an inner part thereof surrounded with the sealing portion 22 thereof. One end (end at the left in FIG. 15) of the body 21 is connected with the other end of the tube 91 communicating with the accommodating portion 23. The capacity of the bag 20 is not limited to a specified one but determined in consideration of various conditions such as the spatial volume (in other words, capacity) of the lumen of the tubes forming the circuit. It is favorable to set the capacity of the bag 20 to 10-100 ml and more favorable to 20-50 ml. If the capacity of the bag 20 is less than the lower limit of the above-described range, the bag 20 cannot accommodate a predetermined collected amount of blood when the spatial volume of the lumen of the tube forming the circuit is comparatively large. On the other hand, if the capacity of the bag 20 is more than the upper limit of the above-described range, the blood collecting apparatus 100 is caused to be large and cannot be operated easily.

The sealing member (in other words, second duct-sealing means) 93 is provided at a portion of the tube 91. The construction of the sealing member 93 will be described in detail later.

A clamp (in other words, clamping member) 95 serving as the second duct-sealing member is provided between the sealing member 93 of the tube 91 and the bag 20. Preferably, the clamp 95 is positioned proximately to the bag 20. The blood collecting apparatus of the eighth embodiment has the two different-type second duct-sealing members 93 and 95.

One end of the flexible tube 96 communicating with the accommodating portion 23 is connected with the other end (in other words, end at the right in FIG. 15) of the body 21. A sampling port (in other words, connector) 71 is connected with the other end of the tube 96. The construction of the sampling port 71 will be described later. A main part of the second duct is constituted of the lumen of each of the tubes 96 and 91.

In the blood collecting apparatus 100, the tube 96 is connected with the bag 20 such that the tube 96 and the tube 91 are located in opposite sides with respect to the bag 20. However, in the blood collecting apparatus of the present invention, the positional relationship between the side at which the tube 96 is connected with the bag 20 and the side at which the tube 91 is connected therewith is not limited to the above-described one. For example, the tube 96 may be connected with the bag 20 at the same side (left in FIG. 15) as that at which the tube 91 is connected therewith. Further, in the blood collecting apparatus of the present invention, the sampling port 71 may be directly connected with the bag 20 at its left end in FIG. 15 or at its right end in FIG. 15.

It is preferable to set the area of the cross-sectional surface of the duct of each of the tubes 91, 96 smaller than that of the cross-sectional surface of the tube 15. That is, it is preferable to set the inner diameter of the tubes 91, 96 smaller than that of the tube 15 to allow collected blood to be left in a small amount in the tubes 91, 96 in introducing the collected blood into the blood collecting bag 10, as will be described later.

It is preferable to set the tube 96 shorter than the tube 91. In particular, it is preferable to set the length of the tube 96 in such an extent that air inside the tube 96 does not have a substantial influence. That is, it is preferable to install the bag 20 in the vicinity of the sampling port (in other words, blood take-out port) 71.

It is preferable to put an anticoagulant agent in the blood collecting bag 10 in advance. Normally, the anticoagulant agent is a liquid. An ACD-A liquid, a CPD liquid, and a CPDA-1 liquid, a heparin sodium liquid, and the like can be used as the anticoagulant agent. The amount of the anticoagulant agent is appropriately determined according to an amount of blood to be collected.

The sheet material composing the blood collecting bags 10 and 20 and the material composing the tubes 15, 61, 91, and 96 will be described below.

[1] Blood Collecting Bag 10

The composition, characteristic, and the like of the sheet material composing the body 11 of the blood collecting bag 10 are not limited to specified ones.

In this case, as the sheet material composing the blood collecting bag 10, soft polyvinyl chloride or materials containing the soft polyvinyl chloride as their main component can be preferably used. For example, a copolymer containing the soft polyvinyl chloride as its main component and a small amount of macromolecular material, a polymer blend, a polymer alloy, and the like can be used.

As the plasticizer for the soft polyvinyl chloride, dioctylphthalate (DEHP, di(2-ethylhexyl)phthalate) and di(n-decyl)phthalate(DnDP) can be preferably used It is favorable to contain the plasticizer in the sheet material at 25-50 wt % and more favorable at 30-40 wt %.

The above-described sheet materials can be manufactured by a method described below.

Using a kneader, materials are kneaded sufficiently. Then, a kneaded material is extruded through a T-shaped die or a circular die. Then, a resulting flat sheet-shaped material is processed into a desired shape/form by sequentially performing the steps of thermoforming, blowing, drawing, cutting, and sealing (fusing) of the edge thereof.

In order to prevent blocking from occurring between sheets (base material), it is possible to roughen (emboss) the surface of each sheet or add or apply a blocking-preventing agent, a slip agent or the like to the materials.

[2] Bag 20

The composition, characteristic, and the like of the sheet material composing the body 21 of the bag 20 are not limited to specified ones. For example, materials similar to the sheet material of the blood collecting bag 10 may be used to form the bag 20. In this case, the kind of sheet material to be prepared can be reduced, which is advantageous in manufacturing the bag 20.

[3] Tubes 15, 61, 91, and 96

As the material of the tubes 15, 61, 91, and 96, thermoplastic elastomers or thermoplastic flexible resin such as soft polyvinyl chloride, polyethylene, polypropylene, ethylene-vinyl acetate copolymer, styrene-butadiene-styrene copolymer, and materials containing the thermoplastic elastomers or the thermoplastic flexible resin. The soft polyvinyl chloride and a material containing the soft polyvinyl chloride as its main component are preferable.

The tubes 15, 61, 91, and 96 made of the soft polyvinyl chloride can be handled easily because they are flexible and pliable and can be suitably sealed with a clamp or the like. Further, because the soft polyvinyl chloride is compatible with the sheet material of the bags 10 and 20, the tube made of the soft polyvinyl chloride and the sheet material of the bags 10 and 20 can be fused or bonded to each other at a high degree. Furthermore, the tube made of the soft polyvinyl chloride has a high degree of airtightness. In addition, the tube made of the soft polyvinyl chloride is durable for centrifuging operation and preferably maintains sterility. The kind of plasticizer to be used for the tubes is not specified. The content thereof is also not specified.

The sizes such as the inner and outer diameters of the tubes 91, 96 are not specified. But if the inner diameter thereof is too large or the thickness thereof is too small, i.e., if the ratio of outer diameter to inner diameter is small, the tubes 91, 96 are likely to be flatly deformed when high pressure-steam sterility is performed. This is because the tubes 91, 96 are soft and sealed with the sealing member 93 and a cap 76 that will be described later.

If the inner diameter of each of the tubes 91, 96 is comparatively large, the spatial volume (volume) of the lumen of each of the tubes 91, 96 is large accordingly. Consequently, blood loss may occur because of the large spatial volume when collection of an initial flow blood or an initial introduced blood and subsequent blood collection are performed.

As a measure for solving the problem of the volume inside each of the tubes 91, 96, it is conceivable to adopt a method of using the tubes 91, 96 having small inner and outer diameters. But there is a limitation in the reduction of the outer diameter of each of the tubes 91, 96 because it is necessary to connect (join) the tubes 91, 96 with other members. Further, the method is incapable of preventing deformation of the tubes 91, 96 sufficiently in the high pressure-steam sterilization.

Accordingly, to solve such a problem effectively, it is favorable to set the inner diameter of each of the tubes 91, 96 to 0.5-2.0 mm and more favorable to 0.8-1.5 mm. It is also favorable to set the outer diameter thereof to 2-4 times as large as the inner diameter thereof and more favorable to 2.5-3.5 times as large as the inner diameter thereof.

If the inner diameter of each of the tubes 91, 96 is less than the lower limit of the above-described range, blood is prevented from smoothly flowing in the initial blood collection into a vacuum blood collecting tube 85 that will be described later. That is, there is a possibility that the flow rate of the blood is insufficient It is preferable that the flow rate of blood is in the range of 1-5 ml/sec.

The outer diameter of each of the tubes 91, 96 most suitable in the connection thereof with other members is preferably in the range of 4.0-4.5 mm.

The construction of each of the sealing members 17 and 93 will be described below. The constructions of the sealing members 17 and 93 are similar to each other. Thus, the construction of the sealing member 93 will be described below representatively.

FIG. 2 is a longitudinal sectional view showing an example of the construction of the sealing member 93. As shown in FIG. 2, the sealing member 93 comprises a short tube 930 made of a flexible resin such as soft polyvinyl chloride and a cylindrical body 931 which is liquid-tightly inserted into the short tube 930 and whose one end is sealed with a solid columnar portion 932.

One end of the tube 91 positioned at an upper side in FIG. 2 is liquid-tightly connected with the upper end of the short tube 930. One end of the tube 91 positioned at a lower side in FIG. 2 is liquid-tightly connected with the lower end of the short tube 930.

A thin and frail breakable portion 933 is formed on the periphery of the cylindrical body 931. The breakable portion 933 is broken by bending the solid columnar portion 932 together with the short tube 930 with fingers to separate the solid columnar portion 932 from the cylindrical body 931. As a result, the duct of the sealing member 93 is opened.

The cylindrical body 931 is made of hard materials such as hard polyvinyl chloride, polycarbonate, polyester or the like.

Referring to FIG. 2, the upper portion of the solid columnar portion 932 is wedge-shaped. The upper end of the solid columnar portion 932 is widthwise smaller than the outer diameter of the cylindrical body 931 and widthwise larger than the inner diameter of the tube 91. This is because the solid columnar portion 932 does not seal the tube 91 after the solid columnar portion 932 is broken and separated from the cylindrical body 931. As shown in FIG. 2, a groove 935 may be formed on the upper end portion 934 of the solid columnar portion 932 to accelerate the flow of blood.

The construction of the sampling port 71 will be described below. FIG. 3 is a vertical sectional view showing an example of the construction of the sampling port 71. In the description made below, the right side of the sampling port 71 in FIG. 3 is referred to as "front side" and the left side thereof is referred to as "rear side".

As shown in FIG. 3, the sampling port 71 includes a body 73, a plug 77, and a cap 76.

The rear side 732 of the body 73 is liquid-lightly connected with the other end of the tube 96.

The body 73 is substantially cylindrical and has a rib 74 erected from the peripheral surface thereof.

The plug 77 into which a needle can be pierced is fitted on a front end 731 of the body 73. As the needle, it is possible to use a needle (for example, double-headed needle) of a blood collecting tool for a vacuum blood collecting tube, a syringe or the like.

The cap 76 to cover the plug 77 is installed on the body 73 at its front side. A blood take-out port is formed at a front portion of the body 73 such that the blood take-out port is proximate to the plug 77.

The body 73 and the rib 74 are made of hard materials such as hard polyvinyl chloride, polycarbonate, polyester or the like.

The material composing the plug 77 is selected from materials into which a blood collecting needle can be pierced comparatively easily. For example, rubber materials such as natural rubber, isoprene rubber, butyl rubber, silicone rubber, urethane rubber, acrylic rubber, and butadiene rubber, styrene-butadiene rubber can be preferably used.

As the material composing the cap 76, rubber materials such as natural rubber, isoprene rubber, butyl rubber, silicone rubber, urethane rubber, acrylic rubber, and butadiene rubber, styrene-butadiene rubber can be preferably used.

As shown in FIG. 4, a holder (in other words, blood collecting tool for vacuum blood collecting tube) 82 of the vacuum blood collecting tube (in other words, vacuum blood collecting vessel) 85 is connected with the sampling port 71 to allow an initial flow blood or an initial introduced blood (in other words, initial flow of collected blood) to be collected by the vacuum blood collecting tube 85 through the holder 82.

The vacuum blood collecting tube 85 includes a body 86 and a rubber plug 87 fitted on the body 86. The interior of the vacuum blood collecting tube 85 is vacuum or in a pressure-reduced state.

The holder 82 comprises a cylindrical body 83 having a bottom and a double-headed needle 84 provided coaxially with the body 83.

In this case, a member (in other words, lure adapter 841) having a male screw formed thereon is fixed to the double-headed needle 84. A female screw engaging the male screw is formed at the center of the bottom portion of the body 83 (left end of body 83 in FIG. 4). The double-headed needle 84 is removably fixed to the body 83 by engaging the male and female screws each other.

The length of the double-headed needle 84 at its left side in FIG. 4 is so set that it can be pierced sufficiently into the plug 77. The length thereof at its right side is also so set that it can be pierced sufficiently into the rubber plug 87.

Although not shown in FIG. 4, it is possible to form an elastic covering member covering the double-headed needle 84 at least one side of the lure adapter 841 to prevent blood from leaking from the double-headed needle 84.

With reference to FIGS. 15 and 4, the operation of the blood collecting apparatus 100, namely, the blood collecting method that is carried out by using the blood collecting apparatus 100 will be described below.

As shown in FIG. 4, the cap 76 is removed from the body 73 of the sampling port 71. Then, the double-headed needle 84 of the holder 82 is pierced into the plug 77 of the sampling port 71 and penetrated therethrough to install the holder 82 on the sampling port 71.

Then, the blood collecting bags 10 and 20 of the blood collecting apparatus 100 are installed at a position, respectively below the position at which the blood collecting needle 152 is pierced into the donor.

Then, as shown in FIG. 15, the tube 15 is sealed with the clamp 16 to close (intercept) the duct thereof. The clamp 95 is opened to open the portion of the duct of the tube 91 between the sealing member 93 and the bag 20.

Then, the cap 153 is removed from the hub 151 to pierce the blood collecting needle 152 into the vein (in other words, blood vessel) of the donor. When it is confirmed that the blood collecting needle 152 is in the vein, the hub 151 is fixed with a tape. Then, the breakable portion 933 of the sealing member 93 is broken to separate the solid columnar body 932 from the cylindrical body 931 to open the duct of the sealing member 93.

Thereby, the initial flow blood flows into the tube 91 through the blood collecting needle 152, a part of the tube 15 (in other words, the part between the blood collecting needle 152 and the branch connector 92), and the branch connector 92, thus being introduced into the accommodating portion 23 of the bag 20. In this case, the duct of the tube 15 is intercepted with the clamp 16. Thus, the blood flows from the tube 15 to the tube 91 through the branch connector 92.

Before introducing the blood into the bag 20, air inside the tubes 15, 91, and that inside the branch connector 92 are exhausted from the other end of the tube 91 and collected in the bag 20.

Thereby, the pressure inside the tubes 15, 91 and the volume of the lumen of the tubes 15, 91 can be kept substantially constant Thus, it is possible to prevent an excess load from being applied to blood cells. Therefore, it is possible to prevent the blood from hemolyzing.

Further, it does not happen that the blood flows into the branch connector 92 at the side of the clamp 16.

After a predetermined amount of blood is collected in the bag 20, the tube 91 is sealed with the clamp 95 to close (intercept) the duct thereof.

Then, blood collection into the blood collecting bag 10 is started.

In this case, the clamp 16 is opened to open the duct of the tube 15. Consequently, the blood collected from the donor flows through the tube 15, thus being introduced into the blood-accommodating portion 13 of the blood collecting bag 10.

In parallel with the blood collection into the blood collecting bag 10, the blood accommodated in the bag 20 is collected (in other words, sampled) into the vacuum blood collecting tube 85.

In this case, the vacuum blood collecting tube 85 is pressed into the innermost portion of the holder 82, and the double-headed needle 84 of the holder 82 is pierced through the rubber plug 87. As a result, the blood accommodated in the bag 20 flows through the tube 96 and is sucked into the vacuum blood collecting tube 85 and collected therein. After the sampling of the blood into the vacuum blood collecting tube 85 is completed, the vacuum blood collecting tube 85 is extracted from the holder 82.

In performing sampling of the blood into a plurality of the vacuum blood collecting tubes 85, the above-described operation is repeated.

After the blood collection into the vacuum blood collecting tubes 85, namely, the sampling of the blood thereinto terminates, the holder 82 is removed from the sampling port 71. Then, the cap 76 is installed on the body 73 of the sampling port 71.

Because the plug 77 is fitted on the body 73 of the sampling port 71, the plug 77 prevents leak of the blood.

In the blood collection into the blood collecting bag 10, after a predetermined amount of blood is collected thereinto, the blood collecting needle 152 is removed from the blood vessel of the donor. Then, the cap 153 is installed on the hub 151. If necessary, the tubes 91, 15 are fused, respectively with a tube sealer or the like. Then, sealed portions of the tubes 91, 15 are cut off to remove the portion thereof located at the side of the sampling port 71.

In this manner, it is possible to obtain the blood collecting bag 10 accommodating the blood not containing the initial flow blood.

In the case of the above-described bag-connected device, the blood accommodated in the blood collecting bag 10 is centrifuged to separate it into a plurality of blood components such as red blood cells, buffy coat, and blood plasma. Then, the obtained blood components are delivered to a predetermined blood component bag connected with the blood collecting bag 10, according to the normal procedure.

The initial flow blood collected in the vacuum blood collecting tube 85 is discarded or can be used for biochemical examinations of blood serum and examinations of the antibody for virus (for example, AIDS, hepatitis and the like) of infectious disease.

As described above, according to the blood collecting apparatus 100, it is possible to collect not containing an initial part of the initial flow blood having a probability of microbism easily and reliably. Thus, the blood collecting apparatus 1 prevents inclusion of bacteria into collected blood or respective components separated from the collected blood, thus having a high degree of safety.

If the blood collecting apparatus 100 does not have the bag 20, there is a possibility that some of the initial flow blood flows into the branch connector 92 at the side of the clamp 16 and is left therein. In this case, the blood remaining there may enter into the blood collecting bag 10 when the main blood collecting is carried out.

The main reason for the penetration of the blood into the branch connector 92 at the side of the clamp 16 is as follows: Let it be supposed that the blood collecting apparatus 100 does not have the bag 20. In this case, in the collecting of the initial flow blood into the vacuum blood collecting tube 85 by introducing it into the tube 91, the air inside the tubes 15a, 91 has nowhere to escape and thus cannot be exhausted to the outside. Thus, the interior of the portion of the tubes 15a, 91 located between the blood collecting needle 152 and the sampling port 71 cannot be filled with the blood, which causes the interface between the air and the blood is stopped at a portion of the tubes 15a, 91. When the vacuum blood collecting tube 85 is installed on the holder 82 in this state, the air inside the tubes 15a, 91 is sucked into the vacuum blood collecting tube 85 immediately after the vacuum blood collecting tube 85 and the sampling port 71 communicate with each other. As a result, the duct of the tubes 15a, 91 become decompressed rapidly. To restore the decompressed state inside the circuit to a normal pressure, the inside of the circuit is filled with the blood. At this time, the blood also flows into the branch connector 92 at the side of the clamp 16.

Because the blood collecting apparatus 100 has the bag 20 in the portion of the duct (second duct) between the branch connector 92 and the sampling port 71, it is possible to exhaust the air from the tubes 15, 91 and collect it in the bag 20, as described above. Thus, the blood is prevented from being introduced into the branch connector 92 at the side of the clamp 16. Therefore, it is possible to eliminate the initial flow blood reliably.

If the blood collecting apparatus 100 does not have the bag 20, the blood introduced into the vacuum blood collecting tube 85 may hemolyze. The hemolysis may cause sodium and potassium contained in blood serum to be measured at a low accuracy.

The cause of the occurrence of the hemolysis is as follows: As described above, let it be supposed that the blood collecting apparatus 100 does not have the bag 20. In this case, in the collecting of the initial flow blood into the vacuum blood collecting tube 85 by introducing it into the tube 91, the interior of the portion of the tube 15a and the tube 91 located between the blood collecting needle 152 and the sampling port 71 cannot be filled with the blood. When the vacuum blood collecting tube 85 is installed on the holder 82 in this state, the air inside the tube 15a and the air inside the tube 91 are sucked into the vacuum blood collecting tube 85 immediately after the vacuum blood collecting tube 85 and the sampling port 71 communicate with each other. As a result, the duct of the tube 15a and that of the tube 91 become decompressed rapidly. At this time, the tubes 15a, 91 are crushed, depending on the position of the blood collecting needle 152, the degree of softness of blood vessel, and the like. As a result, the sectional area of the duct of the tube 15a and that of the tube 91 are reduced and negative pressure is comparatively large (sucking-caused moving speed of blood is comparatively large). consequently, cells, in particular, red blood cells of the collected initial flow blood are damaged.

Because the blood collecting apparatus 100 has the bag 20 between the branch connector 92 and the sampling port 71, it is possible to prevent the blood hemolyzing, as described above.

It is normal to collect the initial flow blood by sequentially providing the holder 82 with a plurality of the vacuum blood collecting tubes 85. If the blood collecting apparatus 100 does not have the bag 20, the first vacuum blood collecting tubes 85 has a smaller amount of the initial flow blood than a predetermined collectable amount (maximum amount of initial flow blood to be collected by sucking in decompressed state). The shortage of the amount of the initial flow blood affects the number of items to be examined, examination accuracy, workability, and the like in examination adversely.

The main reason for the shortage of the amount of the initial flow blood is as follows: Let it be supposed that the blood collecting apparatus 100 does not have the bag 20. In this case, in the collecting of the initial flow blood into the vacuum blood collecting tube 85 by introducing it into the tube 91, the air inside the tubes 15a, 91 cannot be exhausted to the outside. Thus, the interior of the portion of each of the tubes 15a, 91 located between the blood collecting needle 152 and the sampling port 71 cannot be filled with the blood. When the vacuum blood collecting tube 85 is installed on the holder 82 in this state, the air inside the tubes 15, 91 is sucked into the vacuum blood collecting tube 85 and collected therein.

The blood collecting apparatus 100 has the bag 20 for temporarily accommodating blood in the vicinity of the sampling port 71 of the second duct, and sampling of the blood accommodated in the bag 20 into the vacuum blood collecting tubes 85 is performed. Therefore, even though air inside the tube 96 is sucked into the first vacuum blood collecting tubes 85, the amount thereof is small. Thus, it is possible to allow the amount of the initial flow blood that is to be introduced (in other words, sampled) into the first vacuum blood collecting tubes 85 to be substantially equal to that of the predetermined collectable blood amount.

In the case where the bag 20 is provided on a duct other than the second duct, for example, the third duct branching from the second duct, it is necessary to perform a duct-switching operation in introducing the initial blood flow into the tube 91 and introducing it into the vacuum blood collecting tubes 85. However, in the blood collecting apparatus 100, as described previously, the bag 20 is installed on the second duct. Thus, it is unnecessary to perform the duct-switching operation, which facilitates blood treatment to be performed by using the blood collecting apparatus 100.

Further, because the blood collecting apparatus 100 has the sealing member 93 provided on the tube 91, it is possible to select the time at which a collected initial flow blood starts to flow to the tube 91.

As described previously, the inner diameter of each of the tubes 91,96 is set comparatively small (0.5-2.0 mm), and the thickness thereof is set comparatively large (the outer diameter thereof to 2-4 times as large as the inner diameter thereof) to prevent the tubes 91, 96 from being deformed (crushed) at the time of high pressure-steam sterility.

The blood collecting apparatus of the ninth embodiment of the blood collecting apparatus of the present invention will be described below.

Figure 16:
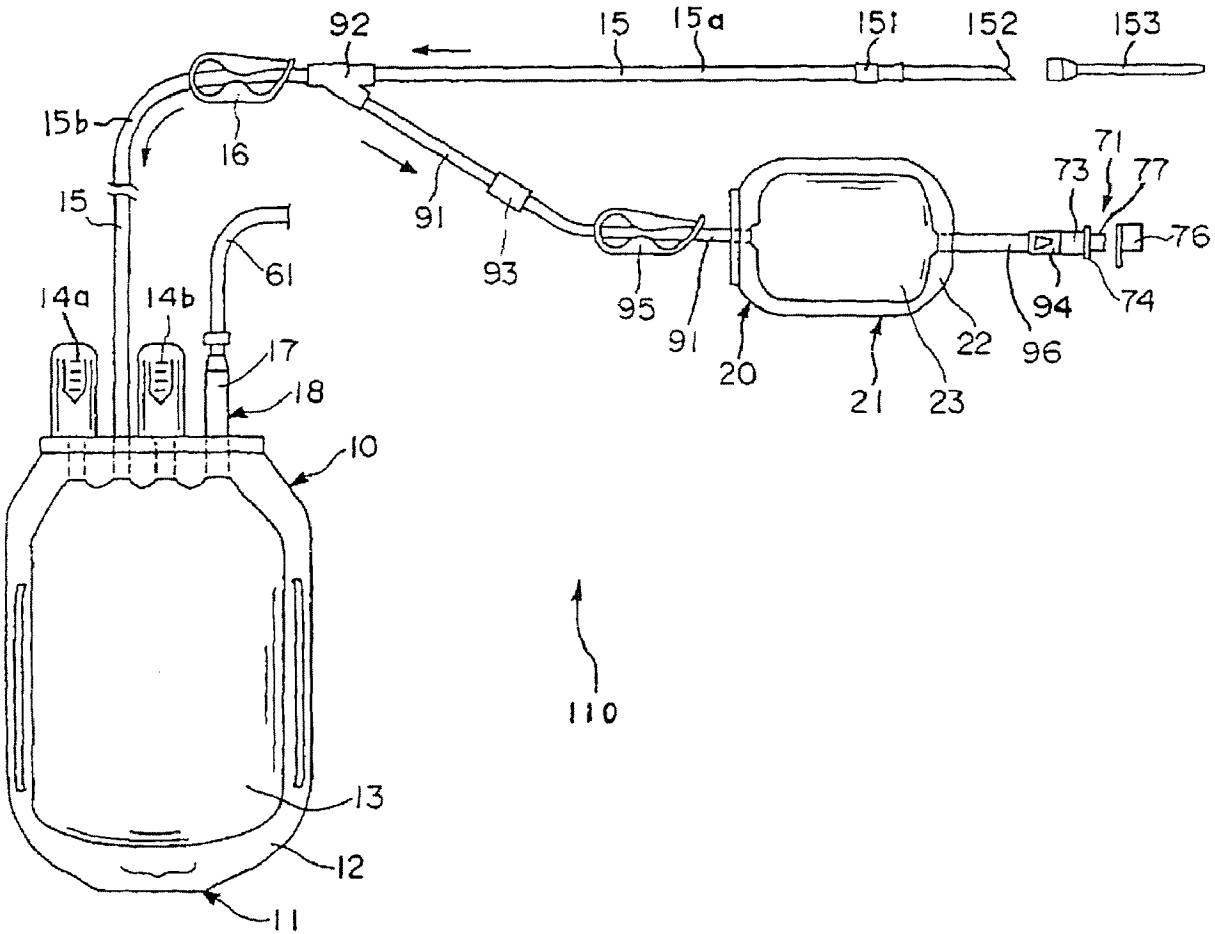
FIG. 16 is a plan view showing a ninth embodiment of the blood collecting apparatus of the present invention.

FIG. 16 is a plan view showing the ninth embodiment of the blood collecting apparatus 110 of the present invention. Description of the constructions of the blood collecting apparatus 110 of the ninth embodiment same as those of the above-described blood collecting apparatus 100 is omitted herein. Thus, only the constructions of the blood collecting apparatus 110 of the ninth embodiment different from those of the blood collecting apparatus 100 will be described below.

As shown in FIG. 16, the blood collecting apparatus 110 has a check valve (in other words, reverse flow prevention member) 94 at a portion between the other end of the tube 96, namely, the end thereof at the right in FIG. 16 and the sampling port 71.

FIG. 10 is a vertical sectional view showing an example of the construction of the check valve (in other words, one way valve) 94. FIG. 11 is a sectional view taken along a line A-A of FIG. 10. In the description made below, the right side in FIGS. 10 and 11 is referred to as "rear side" and the left side therein is referred to as "front side".

As shown in FIGS. 10 and 11, the check valve 94 includes a short tube 940 composed of a flexible resin such as soft polyvinyl chloride and a body 941 made of an elastic material. The body 941 is liquid tightly inserted into the short tube 940 and fixed thereto.

The front end of the short tube 940 is liquid-tightly connected with the sampling port 71. The rear side of the short tube 940 is liquid-tightly connected with an end of the tube 96.

The body 941 has a hollow portion 942 communicating with the tube 96 and forming a part of the blood. A tapered surface 943 is formed on the front end of the hollow portion 942. That is, the vertical length (L) of the front side of the hollow portion 942 decreases gradually from the rear side toward the front side.

A pair of plate-shaped opening/closing members 944 and 944 is formed at the front end of the body 941. The opening/closing members 944 and 944 are in close contact with each other owing to their elastic and restoring forces, thus closing the duct of the check valve 94. When blood flows from the front side to the rear side, the pressure of the blood is applied to the peripheral surface of the opening/closing members 944 and 944, thus acting to bring them into contact each other closely. Thus, the blood does not flow from the front side to the rear side.

When blood flows from the rear side to the front side, a predetermined pressure of the blood is applied to the front end of the tapered surface 943, thus acting to move the opening/closing members 944 and 944 away from each other. As a result, the duct of the check valve 94 is opened, thus flowing the blood from the rear side to the front side.

As the material composing the body 941, rubber materials such as natural rubber, isoprene rubber, butyl rubber, silicone rubber, urethane rubber, acrylic rubber, and butadiene rubber, styrene-butadiene rubber can be preferably used.

The check valve 94 prevents a reverse flow of the blood. That is, the blood does not flow from the sampling port 71 toward the branch connector 92 (the side of the bag 20), but from the branch connector 92 (bag 20) toward the sampling port 71.

Accordingly, in sampling the blood accommodated in the bag 20 into the vacuum blood collecting tube 85, the check valve 94 prevents a reverse flow of the blood, namely, from the sampling port 71 toward to the bag 20.

In the present invention, the position of the check valve 94 is not limited to a specified position as long as it is positioned on the second duct As described above, it is favorable that the check valve 94 is positioned at the side of the sampling port 71 with respect to the bag 20. It is more favorable that the check valve 94 is positioned between the bag 20 and the sampling port 71.

The blood collecting apparatus 110 has the same effect as that of the above-described blood collecting apparatus 100.

The tenth embodiment of the blood collecting apparatus of the present invention will be described below.

Figure 17:
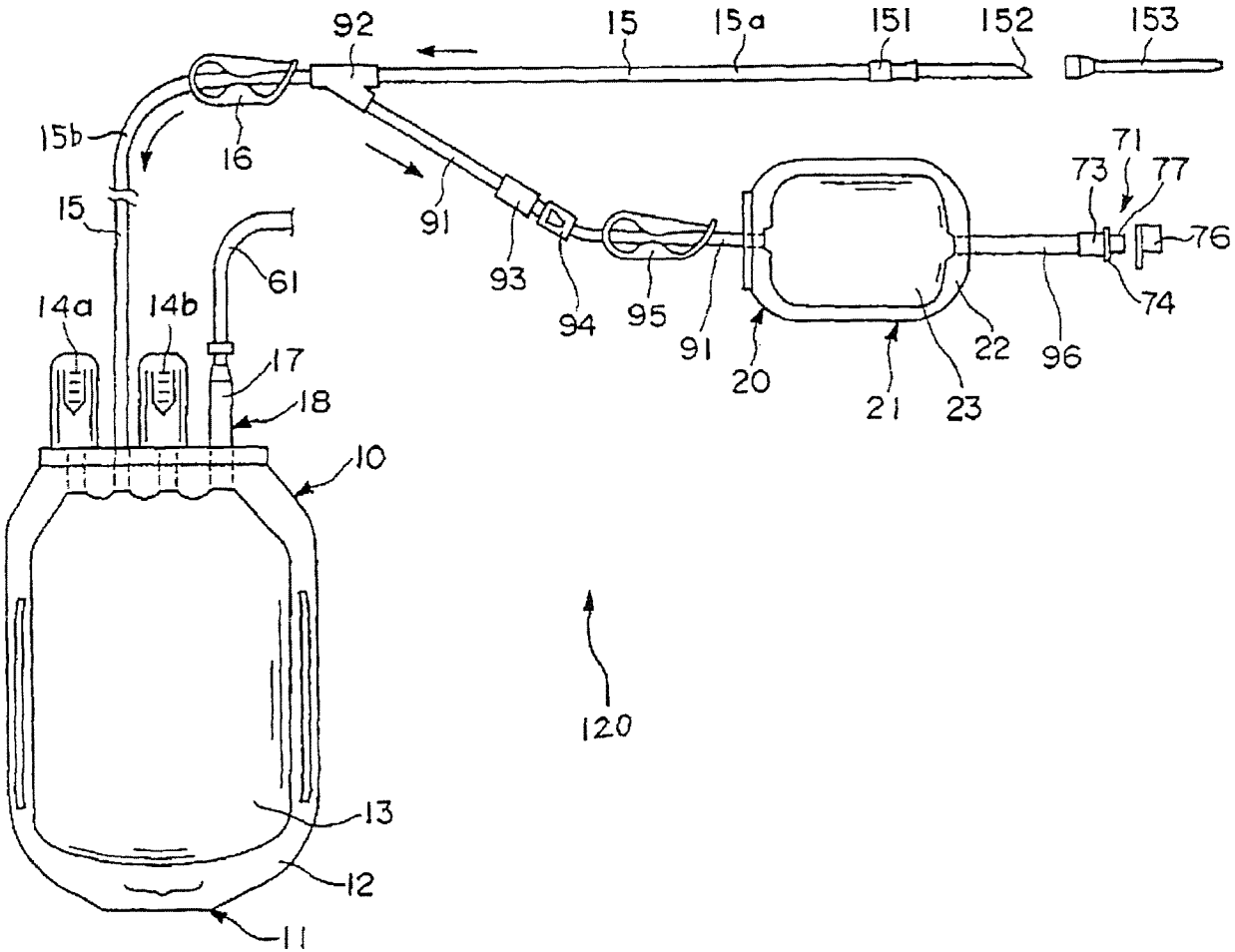
FIG. 17 is a plan view showing a tenth embodiment of the blood collecting apparatus of the present invention.

FIG. 17 is a plan view showing the tenth embodiment of the blood collecting apparatus of the present invention. Description of the constructions of the blood collecting apparatus 120 of the tenth embodiment same as those of the above-described blood collecting apparatus 110 is omitted herein. Thus, only the constructions of the blood collecting apparatus 120 of the tenth embodiment different from those of the blood collecting apparatus 110 will be described below.

As shown in FIG. 17, the blood collecting apparatus 120 has a check valve (in other words, reverse flow prevention member) 94 at a portion of the tube 91, namely, between the sealing member 93 of the tube 91 and the clamp 95.

In introducing blood into the bag 20, the check valve 94 prevents a reverse flow of the blood, namely, from the sampling port 71 toward the branch connector 92.

The blood collecting apparatus 120 has the same effect as that of the above-described blood collecting apparatus 110.

The 11th embodiment of the blood collecting apparatus of the present invention will be described below.

Figure 18:
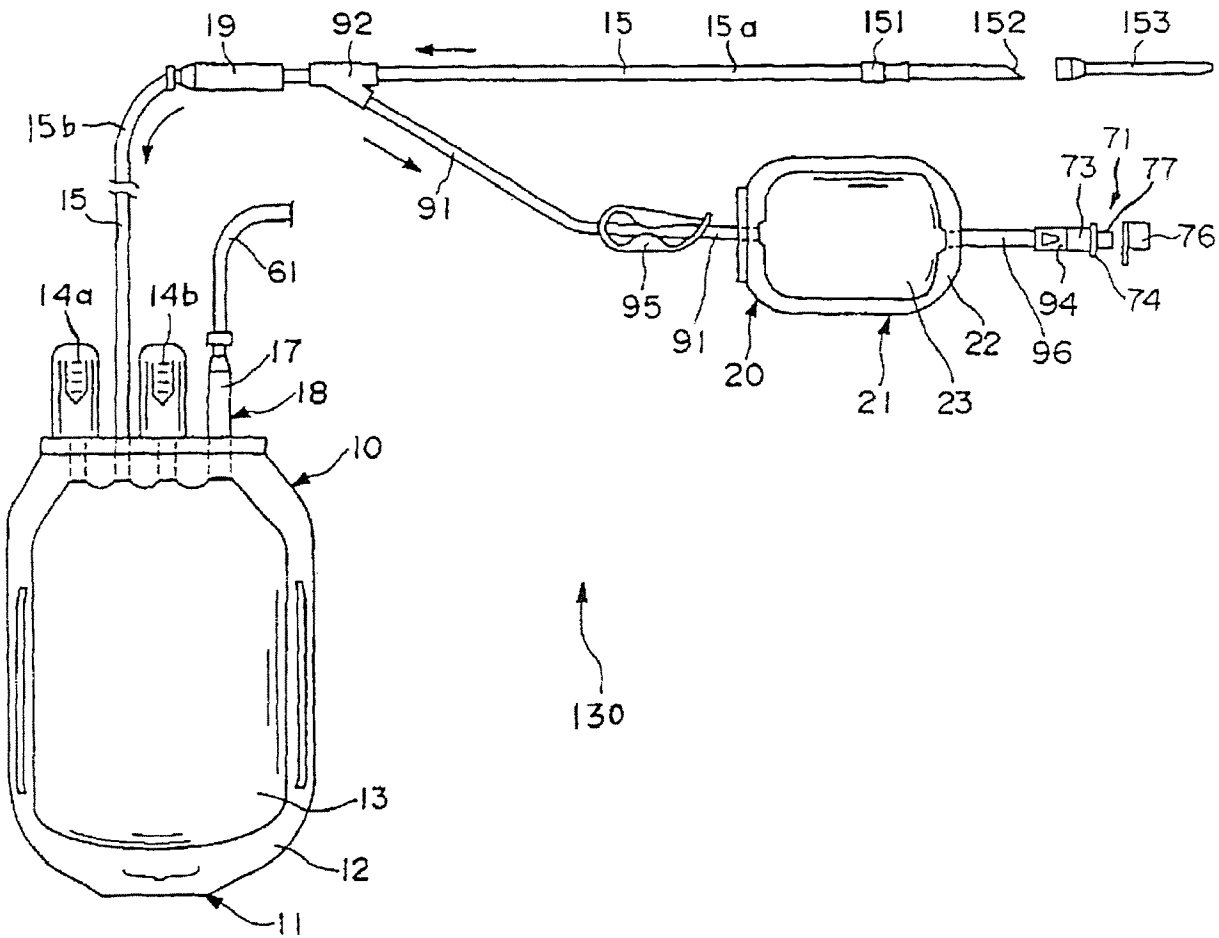
FIG. 18 is a plan view showing an eleventh embodiment of the blood collecting apparatus of the present invention.

FIG. 18 is a plan view showing the 11th embodiment of the blood collecting apparatus 130 of the present invention. Description of the constructions of the blood collecting apparatus 130 of the 11th embodiment same as those of the above-described blood collecting apparatus 110 is omitted herein. Thus, only the constructions of the blood collecting apparatus 130 of the 11th embodiment different from those of the blood collecting apparatus 110 will be described below.

As shown in FIG. 18, in the blood collecting apparatus 130, a first duct-sealing member is composed of a breakable sealing member 19 which is broken to open the first duct. That is, the blood collecting apparatus 130 has the sealing member (in other words, first duct-sealing member) 19 between the branch connector 92 of the tube 15 and the blood collecting bag 10. Preferably, the sealing member 19 is disposed in the vicinity of the branch connector 92.

It is possible to use the sealing member 19 having a construction similar to that of the sealing member 93.

Similarly to the blood collecting apparatus 110, the blood collecting apparatus 130 has the check valve (in other words, reverse flow prevention member) 94 between the other end of the tube 96, namely, the end thereof at the right in FIG. 18 and the sampling port 71. In sampling the blood accommodated in the bag 20 into the vacuum blood collecting tube 85, the check valve 94 prevents a reverse flow of the blood, namely, from the sampling port 71 toward the bag 20.

The blood collecting apparatus 130 has the same effect as that of the above-described blood collecting apparatus 110.

EXAMPLES

The examples of the blood collecting apparatus of the present invention will be described below.

Example 1

The blood collecting apparatus 1 shown in FIG. 1 was prepared. Two soft polyvinyl sheets were used as the material of the flexible resin bag 20. They were laminated on each other and the peripheral edges thereof were fused to each other. The bag 20 had a capacity of 20 ml. Using the blood collecting apparatus 1 and the method previously described, air inside the tube 15a positioned at the side of the blood collecting needle and air inside the tube 91 were introduced into the bag 20 by introducing an initial flow blood. Then, an initial part of the initial flow blood was collected in the vacuum blood collecting tube 85. Then, 200 ml of blood was collected in the blood collecting bags 10. The blood sampling capacity of each vacuum blood collecting tube 85 was 10 ml.

Example 2

The blood collecting apparatus 1a shown in FIG. 5 was prepared. The body 43 of the filter 41 provided on the third tube 31 was made of a sintered material containing polypropylene as its main component Using the blood collecting apparatus 1a and the method previously described, air inside the tube 15a positioned at the side of the blood collecting needle and air inside the tube 91 were discharged from the filter by introducing an initial flow blood. Then, an initial part of the initial flow blood was collected in the vacuum blood collecting tube 85. Then, 200 ml of blood was collected by the blood collecting bag 10. The blood sampling capacity of each vacuum blood collecting tube 85 was 10 ml.

Example 3

The blood collecting apparatus 1b shown in FIG. 7 was prepared. As the vent filter 54 of the air vent (in other words, filter) 51 provided at the second branch portion 32, a membrane filter made of polytetrafluoroethylene was used. Using the blood collecting apparatus 1b and the method previously described, air inside the tube 15a positioned at the side of the blood collecting needle and air inside the tube 91 were discharged through the vent filter 54 by introducing an initial flow blood. Then, a initial part of the initial flow blood was collected in the vacuum blood collecting tube 85. Then, 200 ml of blood was collected by the blood collecting bag 10. The blood sampling capacity of each vacuum blood collecting tube 85 was 10 ml.

Comparison Example 1

Except that a blood collecting apparatus did not have the second branch connector 32, the third tube 31, the clamp 33, and the flexible resin bag 20, the blood collecting apparatus had a construction similar to that of the embodiment 1. Using the blood collecting apparatus and a method similar to that of the embodiment 1 except the operation of clamp 33, an initial part of an initial flow blood was collected in the vacuum blood collecting tube 85. Then, 200 ml of blood was collected by the blood collecting bag 10. The blood sampling capacity of each vacuum blood collecting tube 85 was 10 ml.

Comparison Example 2

Except that a blood collecting apparatus did not have the second branch connector 92, the tube 91, the sealing member 93, the branch connector 32, the third tube 31, the clamp 33, and the flexible resin bag 20, the blood collecting apparatus had a construction similar to that of the embodiment 1. Using the blood collecting apparatus and a conventional method, 200 ml of blood was collected by the blood collecting bag 10.

[Test]

In any of the first-third embodiments and comparison examples 1 and 2, a bacterium fluid of Yersinia enterocolitica (buffer and suspension of phosphoric acid, concentration: 100 cfu/ml) was applied to a donor at a predetermined piercing portion thereof with swabs once a day for a week before blood was collected from them. The piercing portions of the donors were not washed for a week before blood was collected therefrom.

The following bacteria culture tests were conducted by using the blood collected in the blood collecting bags used in the first-third embodiments and comparison examples 1 and 2.

(Bacterium-culturing Test)

200 ml of blood accommodated in the blood collecting bag 10 was mixed with a blood conservation liquid accommodated therein. Then, an operation adapter was pierced into an opening 14 of the blood collecting bag 10. Using a syringe and a needle installed thereon, about 50 ml of blood was aseptically collected from a rubber plug of the operation adapter. The blood was injected into glass containers accommodating a culture medium described below to culture it.

After culturing 25 bloods (25 donors) in a condition described below, the number of the bloods having bacteria was examined. The culture medium and the culture condition were as follows:

Culture medium: Brain Heart Infusion w/PAB and $CO_2$, Under Vacuum (manufactured by Difco Corp.)

Culture amount 50 ml

Culture temperature: 25-30° C.

Observation time period (culture time period): 10 days

The result of the bacterium culture test is shown in table 1 below.

TABLE 1

| | Number of bloods (Number of donors) | Number of Bacterium-Detected Bloods |
|---|---|---|
| Example 1 | 25 | 0 |
| Example 2 | 25 | 0 |
| Example 3 | 25 | 0 |
| Comparison example 1 | 25 | 5 |
| Comparison example 2 | 25 | 5 |

In the first-third embodiments, in the introduction of an initial flow blood into each vacuum blood collecting tube, the tube in the range from the blood collecting needle to the sampling port was substantially filled with blood. Because the initial flow blood was collected into each vacuum blood collecting tube installed on the holder, it did not occur that the blood flowed to the branch connector 92 at the side of the clamp 16. Thus, blood collected from the donor did not contain the initial flow blood. Therefore, as indicated in table 1, the number of bacterium-detected bloods was zero.

On the other hand, because in comparison example 2, collected blood contained the initial flow blood, many collected bloods contained bacteria.

In comparison example 1, because air inside the tube could not be exhausted to the outside when an initial flow blood was introduced into a vacuum blood collecting tube, the tube in the range from the blood collecting needle to the sampling port could not be filled with the blood. Thus, immediately after the vacuum blood collecting tube was installed on the holder, the inside of the circuit was filled with blood to restore a decompressed state to a normal pressure state. At that time, in some cases, the initial flow blood flowed into the branch connector 92 at the side of the clamp 16, thus mixing with collected blood. Therefore, it was impossible to make the number of bacterium-detected bloods zero.

[Hemolysis Test]

Table 2 indicates the degree of hemolysis (number of detected hemolysis) of each collected blood introduced into the vacuum blood collecting tube 85 of each of first-third embodiments and the comparison examples 1 and 2 and average values of the amounts of the initial flow blood introduced into the vacuum blood collecting tubes 85.

The degree of hemolysis of the initial flow of each collected blood was examined as follows: After blood coagulated, blood serum was centrifuged at 3000 rpm for 10 minutes to visually observe the tone of each blood serum. According to the tone of red, the degree of homolysis of the initial flow of each collected blood was determined by using the following three levels, namely, not hemolyzed (level 0), slightly hemolyzed (level 1), and hemolyzed (level 2).

Not hemolyzed (level 0): Tone of red was not observed.

Slightly hemolyzed (level 1): Tone of red was observed in a slight degree.

Hemolyzed (level 2): Tone of red was observed.

"Slightly hemolyzed" (level 1) was also regarded as "hemolyzed" cases. The number of detected "hemolyzed" cases was determined.

TABLE 2

| | Number of Bloods (Donors) | Number of Hemolysis (Visual) | Sampling Blood Volume Average (Graduated Cylinder) |
|---|---|---|---|
| Example 1 | 25 | 0 | 9.8 ml |
| Example 2 | 25 | 0 | 9.8 ml |
| Example 3 | 25 | 0 | 9.8 ml |
| Comparison Example 1 | 25 | 2 | 6.5 ml |

In the first-third embodiments, in the introduction of an initial flow blood into each vacuum blood collecting tube, the tube in the range from the blood collecting needle to the sampling port was substantially filled with blood. Because the initial flow blood was collected into each vacuum blood collecting tube installed on the holder, an excess load was not applied to blood. Thus, the blood did not hemolyze as indicated in table 2 below. That is, in the first-third embodiments, slight degree of hemolysis (level 1) and hemolysis (level 2) were not observed.

In the first-third embodiments, in the introduction of the initial flow blood into each vacuum blood collecting tube, each vacuum blood collecting tube was installed on the holder, with the tube in the range from the blood collecting needle to the sampling port being substantially filled with blood. Thus, as indicated in table 2 below, the amount of the initial flow blood was not reduced.

On the other hand, in comparison example 1, hemolysis was observed. That is, slight hemolysis (level 1) was observed in two glass containers. In the comparison example 1, the inside of the tube in the range from the blood collecting needle to the sampling port could not be filled with blood. Thus, immediately after the vacuum blood collecting tube was installed on the holder, air inside the tube was sucked thereinto. Consequently, the interior of the tube was decompressed and thus the tube was crushed. Thus, it is assumed that when blood flowed through the tube, red blood cells were damaged.

In comparison example 1, the initial flow blood was introduced into the vacuum blood collecting tube, without the inside of the tube in the range from the blood collecting needle to the sampling port being filled with blood. Thus, air inside the tube was sucked into the vacuum blood collecting tube and collected therein. Consequently, the amount of the initial flow of collected blood was reduced by 3.5 ml corresponding to the spatial volume of the length (35 cm) of the tube.

Example 4

The blood collecting apparatus 100 shown in FIG. 15 was prepared. The bag 20 had a capacity of 20 ml. Using the blood collecting apparatus 100 and the method previously described, an initial flow blood was collected in the bag 20. Then, 200 ml of blood was collected in the blood collecting bag 10, and an initial flow blood accommodated in the bag 20 was collected (sampled) into the vacuum blood collecting tube 85. The blood sampling capacity of the vacuum blood collecting tube 85 was 10 ml.

Example 5

The blood collecting apparatus 110 (capacity of bag 20 was 20 ml) shown in FIG. 16 was prepared. As in the case of the example 1, using the above-described method, 200 ml of blood was collected in the blood collecting bag 10, and an initial flow blood was collected (sampling) into the vacuum blood collecting tube 85. The blood sampling capacity of the vacuum blood collecting tube 85 was 10 ml.

Example 6

The blood collecting apparatus 120 (capacity of bag 20 was 20 ml) shown in FIG. 17 was prepared. As in the case of the example 1, using the above-described method, 200 ml of blood was collected in the blood collecting bag 10, and an initial flow blood was collected (sampling) into the vacuum blood collecting tube 85. The blood sampling capacity of the vacuum blood collecting tube 85 was 10 ml.

Example 7

The blood collecting apparatus 130 (capacity of bag 20 was 20 ml) shown in FIG. 18 was prepared. As in the case of the example 1, using the above-described method, 200 ml of blood was collected in the blood collecting bag 10, and an initial flow blood was collected (sampling) into the vacuum blood collecting tube 85. The blood sampling capacity of the vacuum blood collecting tube 85 was 10 ml.

Comparison Example 3

Except that the blood collecting apparatus of the comparison example 3 did not have the bag 20 and the clamp 95, the blood collecting apparatus had a construction similar to that of the blood collecting apparatus of the example 4. Using the blood collecting apparatus, an initial flow blood was directly collected (sampling) into the vacuum blood collecting tube 85. Then, 200 ml of blood was collected in the blood collecting bag 10. The blood sampling capacity of the vacuum blood collecting tube 85 was 10 ml.

Comparison Example 4

Except that the blood collecting apparatus of the comparison example 4 did not have the branch connector 92, the tube 91, the sealing member 93, the clamp 95, and the bag 20, the blood collecting apparatus had a construction similar to that of the blood collecting apparatus of the example 4. Using the blood collecting apparatus and the conventional method, 200 ml of blood was collected in the blood collecting bag 10.

In any of the fourth-seventh embodiments and the comparison examples 3 and 4, a bacterium fluid of Yersinia enterocolitica (buffer and suspension of phosphoric acid, concentration: 100 cfu/ml) was applied to donors at a predetermined piercing portion thereof with swabs once a day for a week before blood was collected from them. The piercing portions of the donors were not washed for a week before blood was collected therefrom.

The following bacteria culture tests were conducted by using the blood collected in the blood collecting bags used in the fourth-seventh embodiments and the comparison examples 3 and 4.

(Bacterium-culturing Test)

200 ml of blood accommodated in the blood collecting bag 10 was mixed with an anticoagulant, an operation adapter was pierced into an opening 14 of the blood collecting bag 10. Using a syringe and a needle installed thereon, about 50 ml of blood was aseptically collected from a rubber plug of the operation adapter. The blood was injected into glass containers accommodating a culture medium described below to culture it.

After culturing 25 bloods (25 donors) in a condition described below, the number of the bloods having bacteria was examined. The culture medium and the culture condition were as follows:

Culture medium: Brain Heart Infusion w/PAB and $CO_2$, Under

Vacuum (manufactured by Difco Corp.)

Culture amount: 50 ml

Culture temperature: 25-30° C.

Observation time period (culture time period): 10 days

The result of the bacterium culture test is shown in table 3 below.

TABLE 3

| | Number of bloods (Number of donors) | Number of Bacterium-Detected Bloods |
|---|---|---|
| Example 1 | 25 | 0 |
| Example 2 | 25 | 0 |
| Example 3 | 25 | 0 |
| Example 4 | 25 | 0 |
| Comparison example 3 | 25 | 10 |
| Comparison example 4 | 25 | 19 |

Study of Result

In the fourth-seventh embodiments, in the introduction of the initial flow blood into the bag 20, air inside the tube could be exhausted into the bag 20. Thereby, it was possible to keep the pressure inside the tube and the volume of the lumen of the tube constant. Thus, it did not occur that the blood flowed to the branch connector 92 at the side of the clamp 16. Thus, the blood collected from the donors did not contain the initial flow blood. Therefore, as indicated in table 3, the number of bacterium-detected bloods was zero.

On the other hand, because in the comparison example 4, the collected blood contained the initial flow blood, many collected bloods contained bacteria.

In the comparison example 3, because air inside the tube could not be exhausted to the outside when the initial flow blood was introduced into the vacuum blood collecting tube, the tube in the range from the blood collecting needle to the sampling port could not be filled with the blood. Thus, immediately after the vacuum blood collecting tube was installed on the holder, the inside of the circuit was filled with blood to restore a decompressed state to a normal pressure state. At that time, in some cases, the initial flow blood flowed into the branch connector 92 at the side of the clamp 16, thus mixing with collected blood. Therefore, it was impossible to make the number of bacterium-detected bloods zero.

Table 4 indicates the degree of hemolysis (number of detected hemolysis) of the collected blood introduced into the vacuum blood collecting tube 85 of each of the fourth-seventh embodiments and the comparison examples 3 and 4 and average values of the amounts of the initial flow blood introduced into the vacuum blood collecting tubes 85.

The degree of hemolysis of the initial flow of each collected blood was examined as follows: After blood coagulated, blood serum was centrifuged at 3000 rpm for 10 minutes to visually observe the tone of each blood serum. According to the tone of red, the degree of hemolysis of the initial flow of each collected blood was determined by using the following three levels, namely, not hemolyzed level 0), slightly hemolyzed level 1), and hemolyzed level 2).

Not hemolyzed level 0): Tone of red was not observed.

Slightly hemolyzed level 1): Tone of red was observed in a slight degree.

Hemolyzed level 2): Tone of red was observed.

"Slightly hemolyzed" level 1) was also regarded as "hemolyzed" cases. The number of detected "hemolyzed" cases was determined.

TABLE 4

| | Number of Bloods (Donors) | Number of Hemolysis (Visual) | Sampling Blood Volume Average (Graduated Cylinder) |
|---|---|---|---|
| Example 1 | 25 | 0 | 9.5 ml |
| Example 2 | 25 | 0 | 9.3 ml |
| Example 3 | 25 | 0 | 9.5 ml |
| Example 4 | 25 | 0 | 9.3 ml |
| Comparison Example 3 | 25 | 13 | 8.0 ml |

Study of Result

In the fourth-seventh embodiments, in the introduction of the initial flow blood into the bag 20, the air inside the tube could be exhausted into the bag 20. Thereby, it was possible to keep the pressure inside the tube and the volume of the lumen of the tube constant Thus, an excessive load was not applied to the blood. Therefore, as shown in table 4, the blood was not hemolyzed. That is, in the fourth-seventh embodiments, the number of slightly hemolyzed level 1) and hemolyzed level 2) cases were not detected.

In the fourth-seventh embodiments, the initial flow blood was accommodated in the bag 20 disposed in the vicinity of the sampling port, and the blood was sampled into the vacuum blood collecting tube. Thus, as shown in table 2, the amount of the initial flow blood was not reduced.

On the other hand, in comparison example 3, hemolysis was observed. That is, slight hemolysis level 1) was observed in 10 glass containers. In the comparison example 3, the inside of the tube in the range from the blood collecting needle to the sampling port could not be filled with blood. Thus, immediately after the vacuum blood collecting tube was installed on the holder, air inside the tube was sucked thereinto. Consequently, the interior of the tube was decompressed and thus the tube was crushed. Thus, it is assumed that when blood flowed through the tube, red blood cells were damaged.

In the comparison example 3, the initial flow blood was introduced into the vacuum blood collecting tube, without the inside of the tube in the range from the blood collecting needle to the sampling port being filled with blood. Because sampling was performed, with the vacuum blood collecting tube installed on the holder, the air inside the tube was sucked into the vacuum blood collecting tube and collected therein. Consequently, the amount of the initial flow of collected blood was reduced by 2 ml corresponding to the spatial volume of the length (30 cm) of the tube.

The embodiments of the blood collecting apparatus of the present invention have been described with reference to the drawings. The present invention is not limited to the embodiments, but the construction of each part of the blood collecting apparatus of each embodiment can be replaced with a part having a desired construction provided that it has the same function as that of each part of the blood collecting apparatus of each embodiment For example, in the present invention, the constructions (constituent features) of the embodiments may be appropriately combined with one another.

Further, in the present invention, the branch portion may be composed of a multi-plug such as a three-way plug instead of the branch connectors shown in the drawings.

As described above, because the blood collecting apparatus of the present invention has the accommodating portion accommodating blood temporarily on the second duct, the initial flow blood is prevented from being left in the branch portion, between the first tube and the second tube, at the side of the blood collecting bag thereof. That is, it is possible to remove the initial flow blood having a probability of microbism easily and reliably from blood collected from a donor. Therefore, it is possible to prevent inclusion of bacteria into the collected blood or respective components separated from the collected blood, thus having a high degree of safety.

When blood is collected (when blood to be examined is collected), it is possible to prevent an excess load from being applied to the blood (prevent cells in blood from being damaged, for example, hemolysis). Thereby, it is possible to collect the initial flow blood in a preferable state.

Further, it is possible to suppress reduction of the amount of collected blood.

Furthermore, the accommodating portion is provided on the second duct. Thus, compared with the accommodating portion provided on a duct other than the second duct (for example, a third duct branching from the second duct), it is easy to perform operations of sampling blood (in collecting blood to be examined).

What is claimed is:

1. A blood collecting apparatus comprising:

a blood collecting needle for collecting blood from a donor;

a blood collecting bag for accommodating collected blood;

a first duct whose one end communicates with said blood collecting bag and other end communicates with said blood collecting needle to introduce said collected blood into said blood collecting bag;

a second duct branching from said first duct through a branch portion and having a blood take-out port; and an accommodating portion, provided on said second duct *to enable collected blood to flow through said second duct and into said accommodating portion*, for accommodating said collected blood temporarily.

2. A blood collecting apparatus comprising:

a blood collecting needle for collecting blood from a donor;

a blood collecting bag for accommodating collected blood;

a first duct whose one end communicates with said blood collecting bag and other end communicates with said blood collecting needle to introduce said collected blood into said blood collecting bag;

a second duct branching from said first duct through a branch portion and having a blood take-out port; and an accommodating portion, provided on a second duct at a portion between said branch portion and said blood take-out port *to enable collected blood to flow through said second duct and into said accommodating portion*, for accommodating said collected blood.

3. A blood collecting apparatus according to claim 1, wherein said accommodating portion comprises a flexible resin bag.

4. A blood collecting apparatus according to claim 1, wherein a capacity of said accommodating portion is in the range of 10-100 ml.

5. A blood collecting apparatus according to claim 1, wherein said accommodating portion is positioned proximately to said blood take-out port.

[6. A blood collecting apparatus according to claim 1, further comprising a first duct-sealing member capable of intercepting said first duct at a portion between said branch portion and said blood collecting bag.]

[7. A blood collecting apparatus according to claim 2, further comprising a first duct-sealing member capable of intercepting said first duct at a portion between said branch portion and said blood collecting bag.]

[8. A blood collecting apparatus according to claim 6, wherein said first duct-sealing member consists of a breakable sealing member which opens said first duct when said breakable sealing member is broken or a clamp member capable of intercepting or opening said first duct.]

9. A blood collecting apparatus according to claim 1, further comprising a second duct-sealing member capable of intercepting said second duct at a portion between said branch portion and said accommodating portion.

10. A blood collecting apparatus according to claim 2, further comprising a second duct-sealing member capable of intercepting said second duct at a portion between said branch portion and said accommodating portion.

11. A blood collecting apparatus according to claim 9, wherein said second duct-sealing member comprises a breakable sealing member which opens said second duct when said breakable sealing member is broken or a clamp member capable of intercepting or opening said second duct.

12. A blood collecting apparatus according to claim 1, further comprising a reverse flow prevention means, provided on said second duct, for allowing a flow in a direction from said branch portion to said blood take-out port and for preventing a flow in a direction opposite to said direction from said branch portion to said blood take-out port.

13. A blood collecting apparatus according to claim 2, further comprising a reverse flow prevention means, provided on said second duct, for allowing a flow in a direction from said branch portion to said blood take-out port and for preventing a flow in a direction opposite to said direction from said branch portion to said blood take-out port.

14. A blood collecting apparatus according to claim 1, wherein an area of a cross-sectional surface of said second duct is set smaller than an area of a cross-sectional surface of said first duct.

15. A blood collecting apparatus according to claim 1, wherein at least one part of said second duct is constituted of a lumen of a tube; an inner diameter of said tube is set to the range of 0.5-2.0 mm; and an outer diameter of said tube is set to two-four times as large as said inner diameter thereof.

16. A blood collecting apparatus according to claim 1, wherein said blood take-out port is formed at an end of said second duct.

17. A blood collecting apparatus according to claim 1, wherein said blood take-out port has a needle-pierceable plug.

18. A blood collecting apparatus according to claim 1, wherein said blood take-out port has a holder of a vacuum blood collecting tube.

19. A blood collecting apparatus according to claim 1, wherein said accommodating portion has a tube communicating with the accommodating portion and having said blood take-out port, and said blood take-out port has a holder of a vacuum blood collecting tube.

*20. A blood collecting apparatus according to claim 1, wherein said accommodating portion is positioned proximately to said blood take-out port.*

*21. A blood collecting apparatus comprising:*

*a blood collecting needle for collecting blood from a donor, said blood including initial flow blood obtained from the donor;*

*a blood collecting bag for accommodating collected blood not containing the initial flow blood;*

*a first duct whose one end communicates with said blood collecting bag and other end communicates with said blood collecting needle to introduce said collected blood into said blood collecting bag;*

*a second duct in which said initial flow blood is introduced and branches from said first duct through a branch portion and has a blood take-out port for sampling blood from said initial flow blood introduced into said second duct;*

*an accommodating portion, provided on said second duct to enable collected blood to flow through said second duct and into said accommodating portion, for accommodating the introduced initial flow blood temporarily, and;*

*a first duct-sealing member for intercepting said first duct at a portion between said branch portion and said blood collecting bag and having a breakable sealing member which opens said first duct when said breakable sealing member is broken.*

*22. A blood collecting apparatus according to claim 21, wherein said accommodating portion is provided on a second duct at a position between said branch portion and said blood take-out port.*

*23. A blood collecting apparatus according to claim 21, wherein said accommodating portion comprises a flexible resin bag.*

*24. A blood collecting apparatus according to claim 21, wherein said blood take-out port has a holder configured to hold a vacuum blood collecting tube.*

*25. A blood collecting apparatus according to claim 21, further comprising a tube communicating with the accommodating portion and having said blood take-out port, and said blood take-out port comprises a holder configured to hold a vacuum blood collecting tube.*

*26. A blood collecting apparatus according to claim 21, wherein an area of a cross-sectional surface of said second duct is smaller than an area of a cross-sectional surface of said first duct.*

*27. A blood collecting apparatus according to claim 21, wherein said blood take-out port has a needle-pierceable plug.*

*28. A blood collecting apparatus according to claim 21, further comprising a second duct-sealing member for intercepting said second duct at a portion between said branch portion and said accommodating portion.*

*29. A blood collecting apparatus according to claim 28, wherein said second duct-sealing member comprises a breakable sealing member which opens said second duct when said breakable sealing member is broken or a clamp member for intercepting or opening said second duct.*

*30. A blood collecting apparatus comprising:*

*a blood collecting needle for collecting blood from a donor;*

*a blood collecting bag for accommodating collected blood;*

*a first duct whose one end communicates with said blood collecting bag and other end communicates with said blood collecting needle to introduce said collected blood into said blood collecting bag;*

*a second duct branching from said first duct through a branch portion and having a blood take-out port;*

*an accommodating portion, provided on said second duct to enable collected blood to flow through said second duct and into said accommodating portion, for accommodating said collected blood temporarily; and*

*a first duct-sealing member for intercepting said first duct at a portion between said branch portion and said blood collecting bag and having a breakable sealing member which opens said first duct when said breakable sealing member is broken.*

*31. A blood collecting apparatus according to claim 30, further comprising a second duct-sealing member capable of intercepting said second duct at a portion between said branch portion and said accommodating portion.*

*32. A blood collecting apparatus comprising:*

*a blood collecting needle for collecting blood from a donor, said blood including initial flow blood obtained from the donor;*

*a blood collecting bag for accommodating collected blood not containing said initial flow blood;*

*a first duct whose one end communicates with said blood collecting bag and other end communicates with said blood collecting needle to introduce said collected blood into said blood collecting bag;*

*a second duct branching from said first duct through a branch portion and having a blood take-out port for sampling blood from said initial flow blood collected into said second duct;*

*an accommodating portion, provided on a second duct at a portion between said branch portion and said blood take-out port to enable collected blood to flow through said second duct and into said accommodating portion, for accommodating said collected initial flow blood; and*

*a first duct-sealing member for intercepting said first duct at a portion between said branch portion and said blood collecting bag and having a breakable sealing member which opens said first duct when said breakable sealing member is broken.*

*33. A blood collecting apparatus according to claim 32, further comprising a second duct-sealing member capable of intercepting said second duct at a portion between said branch portion and said accommodating portion.*

* * * * *